United States Patent [19]

Klosiewicz

[11] Patent Number: 4,568,660

[45] Date of Patent: * Feb. 4, 1986

[54] CYCLOOLEFIN POLYMERIZATION CATALYST COMPOSITION

[75] Inventor: Daniel W. Klosiewicz, Newark, Del.

[73] Assignee: Hercules Incorporated, Wilmington, Del.

[*] Notice: The portion of the term of this patent subsequent to Sep. 4, 2001 has been disclaimed.

[21] Appl. No.: 672,443

[22] Filed: Nov. 16, 1984

Related U.S. Application Data

[60] Continuation-in-part of Ser. No. 472,684, Mar. 7, 1983, Pat. No. 4,520,187, which is a division of Ser. No. 342,453, Jan. 25, 1982, Pat. No. 4,400,340, and a continuation-in-part of Ser. No. 552,195, Nov. 15, 1983, Pat. No. 4,485,208, which is a division of Ser. No. 378,449, May 14, 1982, Pat. No. 4,436,858.

[51] Int. Cl.⁴ .............................................. C08F 4/62
[52] U.S. Cl. .................................. 502/169; 502/102; 502/117; 556/41; 556/57
[58] Field of Search .................. 502/102, 117, 169; 260/429 R, 429 J

[56] References Cited

U.S. PATENT DOCUMENTS

| | | | |
|---|---|---|---|
| 3,084,147 | 4/1963 | Wilks | 260/93.1 |
| 3,446,785 | 5/1969 | Stafford | 260/93.1 |
| 3,472,245 | 1/1970 | Calderon et al. | 502/117 |
| 3,557,072 | 1/1971 | Vergne et al. | 260/88.2 |
| 3,627,739 | 12/1971 | Devlin | 260/88.2 |
| 3,684,787 | 8/1972 | Nutzel | 260/93.1 |
| 3,798,175 | 3/1974 | Streck et al. | 502/117 |
| 3,873,644 | 2/1975 | Pampus et al. | 260/879 |
| 3,935,179 | 1/1976 | Ofstead | 260/93.1 |
| 3,974,092 | 8/1976 | Streck et al. | 252/429 |
| 3,974,094 | 8/1976 | Streck et al. | 252/429 |
| 4,002,815 | 1/1977 | Minchak | 526/283 |
| 4,020,254 | 4/1977 | Ofstead | 526/128 |
| 4,038,471 | 7/1977 | Castner | 502/117 X |
| 4,136,247 | 1/1979 | Tenney et al. | 526/283 |
| 4,136,248 | 1/1979 | Tenney | 526/283 |
| 4,136,249 | 1/1979 | Tenney et al. | 526/283 |
| 4,178,424 | 12/1979 | Tenney et al. | 526/283 |
| 4,250,063 | 2/1981 | Kotani et al. | 260/252 |
| 4,380,617 | 4/1983 | Minchak et al. | 526/161 |
| 4,400,340 | 8/1983 | Klosiewicz | 264/328.6 |
| 4,418,179 | 11/1983 | DeWitt et al. | 525/249 |
| 4,426,502 | 1/1984 | Minchak | 526/172 |
| 4,436,858 | 3/1984 | Klosiewicz | 524/296 |
| 4,458,037 | 1/1984 | Leach | 521/124 |
| 4,469,809 | 9/1984 | Klosiewicz | 502/117 |
| 4,481,344 | 11/1984 | Newburg | 526/143 |
| 4,485,208 | 11/1984 | Klosiewicz | 524/297 |

FOREIGN PATENT DOCUMENTS

92000 8/1978 Japan .
111399 9/1978 Japan .

OTHER PUBLICATIONS

Takata, et al., J. Chem. Soc., Japan, Ind. Chem. Sect., 69,711 (1966).
G. Dall Asta, et al., Die Makromokekulure Chemie 130, 153 (1969).
Takao Oshika, et al., Bulletin of the Chemical Society of Japan, 41, 211–217 (1968).
Billmeyer, Textbook of Polymer Science, 1962, p. 52.
Treloar, The Physics of Rubber Elasticity, 1975, pp. 142–145.

Primary Examiner—Patrick P. Garvin
Attorney, Agent, or Firm—Dale L. Lovercheck

[57] ABSTRACT

A polymerization catalyst composition including $WCl_mO_n$ and

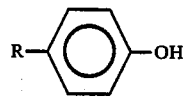

wherein R is an alkyl group having 3 to 20 carbon atoms; m is 4 or 6 and n is 0 or 1. Preferably the composition also includes,

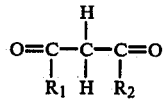

wherein $R_1$ and $R_2$ are independently hydrogen, an alkyl or alkoxy group of form 1 to 5 carbons. Preferably r is 1; m is 4 and R is nonyl and the molar ratio of $WCl_mO_n$ to

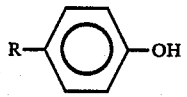

is from about 1:1 to about 1:3.

15 Claims, No Drawings

CYCLOOLEFIN POLYMERIZATION CATALYST COMPOSITION

This application is a continuation-in-part of application Ser. No. 472,684 filed Mar. 7, 1983, now U.S. Pat. No. 4,520,181, which is a division of application Ser. No. 342,453 filed Jan. 25, 1982 and now U.S. Pat. No. 4,400,340 and a continuation-in-part of application Ser. No. 552,195 filed Nov. 15, 1983 and now U.S. Pat. No. 4,485,208 which is a division of application Ser. No. 378,449 filed May 14, 1982, now U.S. Pat. No. 4,436,858.

BACKGROUND OF THE INVENTION

This invention relates to novel polymer product compositions, polymerization feed compositions and monomer purification therefor. In particular, it relates to a crosslinked, high modulus, high impact strength, thermoset polymer of polycycloolefin units which is formed via a metathesis-catalyst system.

Distillation is commonly used in the preparation of polycycloolefins, for example dicyclopentadiene. Various purities of dicyclopentadiene are available. The invention preferably uses economically available purified dicyclopentadiene which is readily polymerized. Purified dicyclopentadiene forms a substantially crosslinked thermoset polymer when polymerized as disclosed herein.

Any good thermoset polymer should meet at least two criteria. It should have desirable physical properties and it should lend itself to easy synthesis and forming. Among the most desirable physical properties for many polymers is a combination of high impact strength and high modulus. A standard test for impact strength is the notched Izod impact test, ASTM No. D-256. For an unreinforced thermoset polymer to have good impact strength, its notched Izod impact should be at least 1.5 ft. lb./in. notch. It is desirable that this good impact strength be combined with a modulus of at least about 150,000 psi at ambient temperature. Thermoset polymers with high impact strength and high modulus find useful applications as engineering plastics in such articles of manufacture as automobiles, appliances and sports equipment. Among the critical factors in the synthesis and forming of a thermoset polymer are the conditions required to make the polymer set up or gel. Many thermoset polymers require considerable time, elevated temperature and pressure, or additional steps after the reactants are mixed before the setting is complete.

A thermoset homopolymer having high impact strength and high modulus has been described by Klosiewicz in U.S. Pat. No. 4,400,340, U.S. Pat. Nos. 4,469,809 and 4,436,858 (with plasticizer) and by Leach in U.S. Pat. No. 4,458,037 (a foam). Characteristics of thermoset polymers include insolubility in common solvents such as gasoline, naphtha, chlorinated hydrocarbons, and aromatics as well as resistance to flow at elevated temperatures.

Work has been done on the metathesis copolymerization of dicyclopentadiene with one or more other monomers to produce soluble copolymers. This copolymer formation has resulted in the production of unwanted insoluble by-products. U.S. Pat. No. 4,002,815, for instance, which teaches the copolymerization of cyclopentene with dicyclopentadiene, describes an insoluble by-product and suggests that the by-product could be a gel of a dicyclopentadiene homopolymer.

Some other work, usually in an attempt to produce soluble polymers, has been done on the metathesis polymerization of dicyclopentadiene. Japanese unexamined published patent applications KOKAI No. 53-92000 and No. 53-111399 disclose soluble polymers of dicyclopentadiene. Several syntheses of soluble polymers of dicyclopentadiene have produced insoluble by-products. Takata et al, J. Chem. Soc. Japan Inc. Chem. Sect., 69, 711 (1966), discloses the production of an insoluble polymerized dicyclopentadiene by-product from the Ziegler-Natta catalyzed polymerization of dicyclopentadiene; Oshika et al, Bulletin of the Chemical Society of Japan, discloses the production of an insoluble polymer when dicyclopentadiene is polymerized with $WCl_6$, $AlEt_3/TiCl_4$ or $AlEt_3/MoCO_5$; and Dall Asta et al, Die Makromolecular Chemie 130, 153 (1969), discloses an insoluble by-product produced when a $WCl_6/AlEt_2Cl$ catalyst system is used to form polymerized dicyclopentadiene.

In U.S. Pat. No. 3,627,739, dicyclopentadiene is gelled with unactivated catalyst and then heated for an hour.

Pampus et al in U.S. Pat. No. 3,873,644 discloses a method of producing graft polymers from a cyclic olefin to obtain thermoplastic products of high impact strength.

Ofstead in U.S. Pat. Nos. 4,020,254 and 3,935,179 disclose metathesis polymerization of cycloolefins to obtain a rubbery polymer. Streck et al in U.S. Pat. Nos. 3,974,092 and 3,974,094 discloses a catalyst for preparation of polyalkenamers. Each discloses polyalkenamers of low reduced melt viscosity. Percent gel obtained using the system of Streck et al is very low. A typical percent gel is about 2 to 6% with 14 being the highest value disclosed. Wilkes in U.S. Pat. No. 3,084,147 discloses thermalpolymerization of dicyclopentadiene. The thermal polymerization is carried out in a nonpolymerizable solvent at about 500° to 550° F.

Stafford in U.S. Pat. No. 3,446,785 discloses a polymerization of olefins. The polymerization discloses the production of a product which is a viscous liquid polymer or a brittle, semi-solid polymer.

Nutzel et al in U.S. Pat. No. 3,684,787 discloses preparation of polyalkenamers. The polymers can be isolated by pouring the solution of polymer into 3 to 5 times its quantity of a solution of a lower alcohol in which an age resister is dissolved. Alternatively, the solution can be introduced into boiling water and the solvent removed with steam. Mensel states in column 1, line 19 that crosslinked products are of no industrial interest. The polymers obtained have a rubber-like character.

Vergne et al in U.S. Pat. No. 3,557,072 discloses plastomers derived from dimethanooctahydronaphthalene and their method of manufacture. Amorphous polymers are obtained in the form of a hard white mass which is washed with methanol and then ground and dried to a white powder.

Tenney et al and Tenney alone in U.S. Pat. Nos. 4,136,247, 4,136,248, 4,136,249 and 4,178,424 disclose ring-opened cycloolefin polymers and copolymers. These polymer products are thermoplastics which can be thermoformed.

Minchak and Minchak et al respectively in U.S. Pat. Nos. 4,002,815 and 4,380,617 each disclose polymerization of cycloolefins to form polymers which may be isolated by precipitation using an alcohol or by steam or hot water stripping. The polymers produced have inherent viscosities from about 0.1 to about 10 and are greater than 90% soluble in solvent. Viscous cements and plastic polymers solidify in from about 30 minutes to 180 minutes. The reaction is short stopped in less than 2 hours by addition of an alcohol. Minchak in U.S. Pat. No. 4,426,502 discloses bulk polymerization of cycloolefins by reaction injection molding in less than about 2 minutes using an organoammonium molybdate or tungstate catalyst.

DeWitt et al in U.S. Pat. No. 4,418,179 discloses impact modification cycloolefins by polymerization using an organoammonium molybdate or tungstate catalysts in the less than 2 minutes using reaction injection molding.

Oshika et al in the Bulletin of the Chemical Society of Japan, line 41, pages 211–217 (1968) discloses ring opening polymerization of norbornene and its derivatives by $MoCl_5$, $WCl_6$ and $ReCl_5$ catalysts. Dark crude polymer is obtained which is dissolved and reprecipitated with methanol.

U.S. Pat. No. 4,002,815 discloses the use of a metathesis-catalyst system which employs a dialkylaluminum iodide, an alkylaluminum diiodide or a mixture of trialkylaluminum compounds with elemental iodine to produce substantially gel-free copolymers of cyclopentene and dicyclopentadiene.

U.S. Pat. No. 4,069,376 discloses the use of a three component catalyst comprised of a soluble tungsten compound, a dialkylaluminum chloride or alkylaluminum dichloride, and a dialkylaluminum iodide or alkylaluminum diiodide to produce substantially gel-free norbornene-dicyclopentadiene copolymers.

U.S. application Ser. No. 526,835 filed Aug. 26, 1983 and now U.S. Pat. No. 4,535,097 and assigned to the same assignee, discloses a cellular crosslinked poly(dicyclopentadiene) which is made with a metathesis-catalyst system. The cellular polymer is made by injecting the catalyst system, which includes an alkylaluminum activator, into a reaction vessel which is preheated, preferably to a temperature from about 100° C. to about 125° C.

Not only is it desirable that the thermoset polymer have high impact strength, but it is also desirable that it be easily synthesized and formed. A reaction injection molding (sometimes hereinafter referred to as RIM) process achieves this second goal by in-mold polymerization. The process involves the mixing of two or more low viscosity reactive streams. The combined streams are then injected into a mold where they quickly set up into a solid infusible mass. For a RIM system to be of use with a particular polymer, certain requirements must be met: (1) the individual streams must be stable and must have a reasonable shelf-life under ambient conditions; (2) it must be possible to mix the streams thoroughly without their setting up in the mixing head; (3) when injected into the mold, the materials must set up to a solid system rapidly; and (4) any additives-fillers, stabilizers, pigments, etc.—must be added before the material sets up. Therefore, the additives selected must not interfere with the polymerization reaction.

Interpenetrating polymer networks (IPNs) are a type of polymer alloy consisting of two (or more) crosslinked polymers. They are more-or-less intimate mixtures of two or more distinct, crosslinked polymer networks held together by permanent entanglements with few, if any covalent bonds between the polymers. The entanglements in IPNs must be of a permanent nature and are made so by self-crosslinking of the two polymers. They are introduced either by swelling a crosslinked polymer with monomer and the crosslinking agent of another polymer, and curing the swollen polymer in situ or by mixing the linear polymer, prepolymers, or monomers in some liquid form solution, or bulk, together with crosslinking agents, evaporating the vehicle (if any), and curing the component polymers simultaneously.

IPNs possess several interesting characteristics in comparison to normal polyblends. Formation of IPNs is the only way to intimately combine crosslinked polymers, the resulting mixture exhibiting (at worst) only limited phase separation. Normal blending or mixing of polymers results in a multiphase morphology due to the well-known thermodynamic incompatibility of polymers. However, if mixing is accomplished simultaneously with crosslinking, phase separation may be kinetically controlled by permanent interlocking of entangled chains.

Molecular and supramolecular perspectives are believed to be important in considering interpenetrating networks. On linked polymer networks intermeshed through molecular chain segment entanglements. These are totally non-separable without chain breaking (i.e. degradation). A semi-interpenetrating network (SIPN) then is a crosslinked network having a non-crosslinked polymer dispersed through it on a molecular scale. These in theory are separable without bond breaking. Neither the interpenetrating network nor the SIPN represents a heterophase polymer structure in a morphological or supramolecular sense.

The supramolecular scale microscopically observable heterophases are present SIPN and IPN. In this context an interpenetrating network is any system of two polymers where the supramolecular structure involves two intermeshed continuous polymer phases irrespective of whether or not they are crosslinked.

Because molecular mixing of dissimilar uncrosslinked polymers is thermodynamically unfavorable (for entropic reasons) it is unusual to form a stable, molecular IPN from two uncrosslinked polymers. They generally will separate into a heterophase polymer system which might or might not be a supramolecular IPN.

The forming of supramolecular interpenetrating networks of two uncrosslinked polymers is called polymer blends. "Coreacted" polymers is a process which results in block copolymers and sometimes results in heterophase polymer systems which could exhibit supramolecular IPN morphology, depending on block length.

SUMMARY OF THE INVENTION

A polymerization catalyst composition including $WCl_mO_n$ and

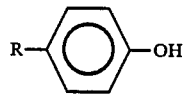

wherein R is an alkyl group having 3 to 20 carbon atoms; m is 4 or 6 and n is 0 or 1. Preferably the composition also includes,

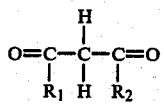

wherein $R_1$ and $R_2$ are independently hydrogen, an alkyl or alkoxy group of form 1 to 5 carbons. Preferably r is 1; m is 4 and R is nonyl and the molar ratio of $WCl_mO_n$ to

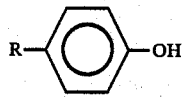

is from about 1:1 to about 1:3.

DETAILED DESCRIPTION OF THE INVENTION

As used herein, unless otherwise specified, percentage of materials are in percent by weight.

As used herein, unless otherwise specified, "solvent" means a fluid in which the monomer or catalyst is readily soluble.

Preferably, the composition used to make the polymers of the present invention have from 0 to about 2 percent solvent. Particularly for making solid (unfoamed) polymer the less solvent present the fewer voids formed in the product. In general, and particularly in the formation of molded noncellular solid polymer, the polymerization mixture is about 88 to 98 percent polycyclic olefin monomer, on a blowing agent free basis. Preferably, the polymerization solution is about 0 to 10 percent elastomer. The solvent present, if any, is probably from the catalyst solution added to the monomer to make to polymerization solution.

Throughout this disclosure, percentages are weight by weight unless otherwise specified.

Cycloolefins, for example, dicyclopentadiene can be polymerized in such a manner that the resulting product is a thermoset homopolymer having high impact strength and high modulus. Dicyclopentadiene, the preferred monomer, is commercially available endo-DCPD (3a,4,7,7a tetrahydro-4,7-methano-1H-indene). The exo-isomer, while not commercially available, can be used just as well. The preferred commercially available material has a purity of 96–97%. Commercially available material should be purified in order to prevent impurities from inhibiting the polymerization. The low boiling fraction should be removed. This can be done by stripping away several percent of the unsaturated four to six carbon atom volatiles, i.e., the volatiles distilled below 100° C. at about 90±3 torr absolute pressure. It is often desirable to purify the starting material even further by treatment with an absorbent such as molecular sieves, alumina or silica gel. Additionally, the water content of the starting material should be below about 100 ppm. The presence of water interferes with polymerization by hydrolysis of both the catalyst and the activator components of the catalyst system. Water can be removed by azeotropic distillation under reduced pressure.

The polymerization of the purified cyclolefin containing at least 50 percent dicyclopentadiene is catalyzed by a two part metathesis-catalyst system. One part contains a tungsten containing catalyst, such as a tungsten halide or tungsten oxy halide, preferably $WCl_6$, $WOCl_4$ or a mixture thereof. The other part contains an activator such as tetraalkyl tin or an alkylaluminum compound. The alkylaluminum compound can be a trialkylaluminum, an alkylaluminum dihalide or a dialkylaluminum halide where the alkyl group contains one to ten carbon atoms. In the preferred activator the alkyl group is octyl.

One part of the catalyst system comprises the tungsten containing catalyst, preferably in solution with dicyclopentadiene monomer. The tungsten compound, if unmodified, will rapidly polymerize the monomer. Consequently, the tungsten compound should first be suspended in a small amount of a suitable solvent. The solvent must not be susceptible to reacting with the tungsten compound. For instance, where a tungsten halide is employed the solvent must not be susceptible to halogenation. Examples of preferred solvents are benzene, toluene, xylene, chlorobenzene, dichlorobenzene, and trichlorobenzene. Sufficient solvent should be added so that the tungsten compound concentration is between about 0.1 and 1.0 mole per liter of solution.

The tungsten compound can be solubilized by the addition of a small amount of an alcoholic or a phenolic compound. Phenolic compounds are preferred. Suitable phenolic compounds include phenol, alkyl phenols, and halogenated phenols, with tert-butyl phenol, tert-octyl phenol and nonyl phenol being most preferred. The preferred molar ratio of tungsten compound/phenolic compound is from about 1:1 to about 1:3. The tungsten compound/phenolic compound solution can be made by adding the phenolic compound to a tungsten compound/organic solvent slurry, stirring the solution and then blowing a stream of a dry inert gas through the solution to remove any hydrogen chloride. Alternatively, a phenolic salt, such as a lithium or sodium phenoxide, can be added to a tungsten compound/organic solvent slurry, the mixture stirred until essentially all the tungsten compound is dissolved, and the precipitated inorganic salt removed by filtration or centrifugation. All of these steps should be carried out in the absence of moisture and air to prevent deactivation of the catalyst.

Stabilization of Catalyst

To prevent premature polymerization of the tungsten compound/monomer solution, which would occur within a matter of hours, from about 1 to about 5 moles of a Lewis base or a chelating agent can be added per mole of tungsten compound. Preferred chelants include acetylacetones, alkyl acetoacetates, where the alkyl group contains from one to ten carbon atoms; preferred Lewis bases are nitriles and ethers such as benzonitrile and tetrahydrofuran. The improvement in the stability and shelf-life of the tungsten compound/monomer solution is obtained whether the complexing agent is added before or after the phenolic compound. When purified cycloolefin, for example dicyclopentadiene is added to this catalyst solution it forms a solution which is stable and has a shelf-life of several months. The other part of the metathesis-catalyst system comprises the activator, as described above, preferably in dicyclopentadiene monomer.

Induction Time Control

Induction time is the period of time between mixing of catalyst, activator and monomer and the exotherm, which indicates the onset of exothermic polymerization.

If an unmodified activator/monomer solution is mixed with the catalyst/monomer solution, the polymerization will initiate spontaneously and instantaneously and the polymer can set up in the mixing head. The onset of polymerization can be delayed by adding a reaction rate moderator to the activator/monomer solution. Ethers, esters, ketones, nitriles and polar cycloolefins can act as moderators for the alkylaluminum compounds. Ethyl benzoate, butyl ether bis(2-methoxyethyl)ether and polar cycloolefin monomers are preferred. The induction time is controlled by varying the specific amount of rate moderator used. The preferred ratio of the alkylaluminum to moderator is from about 1:1.5 to about 1:5 on a molar basis.

Preferably, the polymerization of cycloolefin using activated catalyst to form substantially crosslinked polymerized units of cycloolefin is substantially complete in from about 1 second to about 18 minutes. More preferably, this polymerization is substantially complete in from about 10 seconds to about 10 minutes. Most preferably, the polymerization is substantially complete in from about 15 seconds to about five minutes.

The induction time is also temperature dependent. As the temperature at which the reaction is carried out is increased the induction time will decrease. Consequently, to keep the induction time controlled at higher reaction temperatures a less active formulation of the metathesis catalyst system should be used. One way of reformulating the system is by choice of moderator. Other ways will be readily determinable by one skilled in the art.

What is ultimately required is that when the catalyst system's components are combined, the resulting cycloolefin (for example dicyclopentadiene) to tungsten compound ratio will be from about 500:1 to about 15,000:1 on a molar basis, preferably 2,000:1 and the dicyclopentadiene to alkylaluminum ratio will be from about 100:1 to about 2000:1 on a molar basis, preferably about 200:1 to about 500:1. To illustrate a preferred combination: sufficient dicyclopentadiene is added to a 0.5 molar tungsten containing catalyst solution prepared as described above, so that the final tungsten compound concentration is 0.007 molar. This corresponds to a dicyclopentadiene to tungsten compound ratio of 1000:1. Sufficient dicyclopentadiene is added to the diethylaluminum chloride ($Et_2AlCl$) solution, prepared as described above, so that the alkylaluminum concentration is 0.048M. This corresponds to a dicyclopentadiene to alkylaluminum ratio of 150:1. If these two streams are mixed in a 1:1 ratio, the final ratio of dicyclopentadiene to tungsten compound will be 2000:1, the final ratio of dicyclopentadiene to alkylaluminum will be 300:1 and the final ratio of tungsten compound to alkylaluminum will be about 1:7. The illustrated combination is not the lowest catalyst level at which moldings can be made, but it is a practical level that provides for excess catalyst if impurities in the system consume some of the catalyst components. A higher alkylaluminum level will not only increase costs and residual chlorine levels but may result in a less satisfactory cure. Too low a tungsten compound concentration results in incomplete conversion. A wide range of alkylaluminum activator to tungsten catalyst formulations produce substantially crosslinked polymer products which have good out-of-mold properties such as tear resistance, stiffness, residual odor, and surface properties.

In a preferred synthesis, the polymerized dicyclopentadiene is made and molded via the RIM process. The two parts of the metathesis catalyst system are each mixed with dicyclopentadiene, to form stable solutions which are placed in separate vessels. These vessels provide the source for separate streams. The two streams are combined in the RIM machine's mixing head and then injected into a warm mold where they quickly polymerize into a solid, infusible mass. The invention is not intended to be limited to systems employing two streams each containing monomer. It will be obvious to one skilled in the art that there may be situations where it is desirable to have monomer incorporated in just one stream or to employ more than two streams where the additional streams contain monomer and/or additives.

These streams are completely compatible with conventional RIM equipment. Metathesis catalyzed polymerizations are known to be inhibited by oxygen so it is necessary to store the components under an inert gas but, surprisingly, it is not necessary to blanket the mold with an inert gas. The streams are combined in the mixing head of a RIM machine. Turbulent mixing is easy to achieve because the process involves low viscosity, low molecular weight, rapidly diffusing components. Typically the mixing heads have orifices about 0.032 inch in diameter and a jet velocity of about 400 ft/sec. After being combined the mixture is injected into a mold maintained at 35°-100° C., preferably 50°-70° C. The mold pressure is in the range of about 10-50 psi. A rapid exothermic reaction occurs as the poly(DCPD) sets up. The mold can be opened in as little as 20-30 seconds after the combined streams have been injected. In this short time heat removal is not complete and the polymer is hot and flexible. The polymer can be removed from the mold immediately while hot or after cooling. After the polymer has cooled it will become a rigid solid. The total cycle time may be as low as 0.5 minute.

The substantially crosslinked product has a flexural modulus of at least about 150,000 to 300,000 psi and a notched Izod impact resistance of at least about 1.5 ft. lb./in. notch. The polymer product is low in residual monomer and insoluble in common solvents such as gasoline, naphthas, chlorinated hydrocarbons and aromatics, resistant to flow at temperatures as high as 350° C. and readily releases from the mold.

An important property of the thermoset polymer, which gives rise to these desirable characteristics, is the extent to which the polymer is crosslinked. An indication of the extent of crosslinking is provided by the polymer's swell value. Gel and swell are determined by a modified version of ASTM D-3616. The measurement is made after the polymer is immersed in toluene for two hours at 100° C. Percent swell is defined as swollen polymer weight minus initial polymer weight, divided by initial polymer weight times one hundred. It has been found that the polymerized cycloolefins of this invention have a swell value of less than about two hundred percent. Preferably, the polymerized cycloolefins of the invention have a swell value less than 150 percent. More preferably, the polymer products of the invention have a swell value of less than 100 percent. Preferably, the percent gel is at least 85% by weight of polymerization feed mixture. More preferably, the percent gel is at least 90%. Most preferably, the percent gel is at least 95% by weight.

Billmeyer in the Textbook of Polymer Science (1962) at page 52 discloses that a crosslinked polymer cannot dissolve completely but may swell to many times its original volume by absorbing a liquid with which it is in contact. Swelling occurs for the same reason that a linear polymer dissolves; the addition of solvent affords an increase in entropy. The swollen gel is in fact an elastic rather than a viscous solution. The tendency towards swelling is opposed by an elastic retractive force arising as the chains between network junctions are forced to assume elongated confirmations. The swelling of the gel in pure solvent may be used to measure the second virial coefficient of the crosslinked polymer in that solvent. The change in volume measures the change in activity of the solution and thus, the number-average molecular weight of the polymer. Treloar in the Physics of Rubber Elasticity (1975) at pages 142–145 discloses a relation between swelling and modulus. A relation is expressed between the equilibrium swelling and the degree of crosslinking represented in terms of the molecular weight of the network chains.

Various additives can be included to modify the properties of cycloolefin polymer product of the invention. Possible additives include fillers, pigments, antioxidants, light stabilizers, plasticizers and polymeric modifiers. The disclosure of U.S. Pat. No. 4,436,858 is incorporated herein by reference. Because of the rapid polymerization time the additives must be incorporated before the cycloolefin monomer sets up in the mold. It is often desirable that the additives be combined with one or both of the catalyst system's streams before being injected into the mold. Reinforcing materials can also be charged to the mold cavity, prior to charging the reaction streams, if the fillers are such that the reaction stream can readily flow around them to fill the remaining void space in the mold. It is essential that the additives not adversely affect catalytic activity.

One class of possible additives is reinforcing agents or fillers. These are compounds which can increase the polymer's flexural modulus with only a small sacrifice in impact resistance. Possible fillers include glass, wollastonite, mica, carbon black, talc, and calcium carbonate. It is surprising that, in spite of the highly polar nature of the surfaces of some of these fillers, they can be added without appreciably adversely affecting the polymerization rate. From about 0% to 75% by weight of additives can be incorporated. Preferably from 1 to 40% by weight of additives are incorporated. This and all subsequent percentages are based on the weight of the final product. The addition of fillers which have modified surface properties are particularly advantageous. The exact amount of a particular filler to be used in a particular situation will be easily determinable and will depend on the preferences of the practitioner. The addition of fillers also serves to decrease the mold shrinkage of the product. After a short post cure at 150°–200° C. an unfilled product will shrink from about 3.0 to about 3.5% whereas adding 20–25 wt% filler will decrease the shrinkage to 1.5–2% and adding 33 wt% filler will further decrease shrinkage to about 1%.

Where the filler includes fine particles of a material which is substantially chemically inert to the polymerization of the cycloolefin, this material is believed to act as a heat sink. It thus absorbs the exothermic heat of polymerization. In the presence of an effective amount (for example 10% by weight, of evenly distributed 1/16 inch long milled glass fibers or wollastonite particles) of chemically inert heat sink material the maximum temperature of polymerization is lowered. This is believed to extend the active life of the catalyst so that less than two percent residual monomer is left in the cycloolefin polymer product. Preferably, the quantity, distribution and fineness of the chemically inert heat sink material is effective to result in less than one percent residual monomer in a commercial polymerization. More preferably the quantity, distribution and fineness of the chemically inert heat sink material is effective to result in order of increasing preference in less than 0.9, 0.8, 0.5, 0.3 or 0.05 percent residual monomer in a commercial polymerization. Most preferably the quantity, distribution and fineness of the chemically inert heat sink material is effective to result in less than 0.1 percent residual monomer in a commercial polymerization.

Similarly, low residual monomer polymer products are obtained by controlled reaction of cycloolefin monomer using tungsten compound catalyst and dialkylaluminum chloride activator in an activator to catalyst ratio within the range of from about 2.5:1 to about 6:1. More preferably, the activator to catalyst ratio is from 2.5:1 to about 4:1. Most preferably, the activator to catalyst ratio is from about 3:1 to about 3.5:1 to obtain a polymer product having from about 0.3 to about 1.5 percent by weight residual monomer.

Flame retardant additives may be added to one or more of the monomer feed streams to form polymers which are resistant to burning. For example, on a weight basis a flame retardant mixture of 17 parts of N,N'-ethylene-bis-tetrabromophthalimide, 7 parts $Sb_2O_3$ and 8 parts $NH_4BF_4$ as the flame retardant mixture per 100 parts of dicyclopentadiene imparts a V-0 rating in the UL-94V burn test where UL is an abbreviation for Underwriters Laboratories when mixed with 0.05 parts $WCl_6$ and 0.15 parts of tri-n-octyl aluminum as described herein to form substantially crosslinked polymerized units of dicyclopentadiene. This represents effective flame retardation. The range of weight portions for effective flame retardation is from 8 to 20 parts of N,N'-ethylene-bis-tetrabromophthalimide, from 6 to 15 parts $NH_4BF_4$ and from 3 to 11 parts $Sb_2O_3$ per 100 parts of dicyclopentadiene.

The polymers formed in accordance with the present invention include foams. Foaming is carried out by including a blowing agent as described in U.S. patent application Ser. No. 526,836, (Newburg) the disclosure of which is incorporated by reference.

Since polymerized dicyclopentadiene contains some carbon-carbon unsaturation it may be subject to oxidation. The product can be protected by the incorporation of as much as about 2.0 wt% of a phenolic or amine antioxidant. Preferred antioxidants include 2,6-di-tert-butyl-p-cresol, N,N'-diphenyl-p-phenylene diamine and tetrakis [methylene(3,5-di-t-butyl-4-hydroxy cinnamate)] methane. While the antioxidant can be added to either or both streams, incorporation into the catalyst-/monomer stream is preferred.

A supramolecular IPN is believed to be formed in the embodiments of the present invention in which styrene butadiene rubber is present during the polymerization of dicyclopentadiene as described hereinafter. The addition of an elastomer can increase the polymer's impact strength 5–10 fold with only a slight decrease in flexural modulus. The elastomer can be dissolved in either or both of the DCPD streams in the 5–10 wt% range without causing an excessive increase in the solution viscosity. Useful elastomers may be unsaturated such as styrene-butadiene rubber, polyisoprene, polybutadiene, natural rubber, styrene-isoprene-styrene triblock rubber, styrene-butadiene-styrene triblock rubber, and ethylene-propylene diene terpolymers; or saturated such as polyisobutylene and ethylene-propylene copolymer. It is believed that a saturated elastomer forms a semi-interpenetrating network when present during the polymerization of a cycloolefin, such as dicyclopentadiene. Each of the unsaturated elastomers is believed to form an interpenetrating network with the polymerized units of cycloolefin, such as dicyclopentadiene, when present during the polymerization of the monomer. The amount of elastomer used is determined by its molecular weight and is limited by the viscosity of the streams. The streams cannot be so viscous that adequate mixing is not possible. The Brookfield viscosity of dicyclopentadiene is about 6 cps at 35° C. Increasing the viscosity to between about 300 cps and about 1000 cps improves the mold filling characteristics of the combined streams. An increase in viscosity reduces leakage from the mold and simplifies the use of fillers by decreasing the settling rates of the solids. An example of a preferred polymerization. Where 6 wt% of this additive is incorporated into the streams not only is the viscosity increased to about 300 cps but the impact strength of the final product also increases. Although the elastomer can be dissolved in either one or both of the streams it is desirable that it be dissolved in both. When the two streams have similar viscosities more uniform mixing is obtained.

Monomer Preparation

Preferred monomers are cycloolefins of the norbornene-type and are those defined by the following formulas:

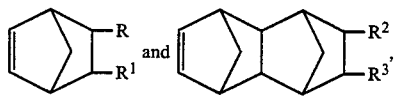

where R and $R^1$ are independently selected from hydrogen, alkyl groups of 1 to 20 carbon atoms, and saturated and unsaturated hydrocarbon cyclic groups formed by R and $R^1$ together with the two ring carbon atoms. $R^2$ and $R^3$ are independently selected from hydrogen and alkyl groups containing 1 to 20 carbon atoms.

Dicyclopentadiene (DCPD) for use in forming substantially crosslinked thermoset polymers which may be formed for example in reaction injection molding (RIM) is required because of high purity. The degree of purity of the DCPD monomer may determine whether the polymerization proceeds at all and whether an acceptable polymer is formed if polymerization occurs.

The highest purity commercial grade of monomer, 97% by weight dicyclopentadiene, is unacceptable for polymerization without purification. Ninety-seven percent by weight dicyclopentadiene can be made acceptable for RIM use by distillation. For example, a column packed with 1-inch Intalox Saddles (10–12 theoretical trays) provides dicyclopentadiene purification with recovery of purified dicyclopentadiene of about 70–75% because the relative volatilities of some of the polymerization inhibitors appear to be very close to that of dicyclopentadiene. Purified dicyclopentadiene substantially completely polymerizes in about ¾ minute or less. Purified dicyclopentadiene is produced by nitrogen sparging 97% by weight dicyclopentadiene followed by treatment with alumina.

Although polymerization inhibitors in crude dicyclopentadiene are still not fully identified, suspected contaminants are polar compounds such as epoxides, alcohols, aldehydes, and some other oxygen-containing compounds. Oxygenated compounds have generally intermediate or high polarity and are adsorbed on alumina or in zeolites.

The major volatile impurities in the 97% pure commercial dicyclopentadiene are isoprene and cis/trans 1,3-pentadiene, which do not affect the polymerization, but are undesirable for a reaction injection molding process. The volatile compounds can be removed simply by stripping.

Adsorption, in both mixing contact and fixed bed (percolation), are used. The contact method consists of mixing the dicyclopentadiene to be purified with an adsorbent in a container with inert atmosphere under controlled time and temperature conditions. Agitation is accomplished by adding a magnetic stirring bar to the container. In the fixed bed method, the DCPD is purified by passing it through a column packed with an adsorbent under controlled flow and temperature conditions.

One of the most effective adsorbent for DCPD purifications is Linde 10 A molecular sieve (Union Carbide Type 13X M.S.). This adsorbent rapidly turns to a dark chocolate brown color when 97% by weight dicyclopentadiene is added. Most of the dark color can be extracted from the molecular sieves by acetone or hexane. IR analyses indicated that the color extracts are consisted mainly of oxygenated compounds and some unsaturated cis-olefin. Activated alumina is also effective in removing catalysis poisons from dicyclopentadiene.

A series of mixing tests are conducted to compare the effectiveness of various adsorbents. The results are shown in Table I.

TABLE I

|  | Polymerization delay time in seconds |
| --- | --- |
| Alumina | 53–65 |
| Zeolite (8–9 A pour size) | 84 |
| (4–5 A pour size) | 85 |
| Linde Mole Sieve, 4 A | 98 |
| 5 A | 65 |
| ED-3100 | 55 |
| 10 A | 40 |

Polymerization delay time is measured after 90 minutes of mixing. DCPD used for mixing is 4% topped 97% by weight DCPD (delay time—2.5 minutes).

Percolation Tests and Mileage

Dicyclopentadiene is purified by passing it through a 1-in diameter×4-ft. column packed with various adsorbents. The column is maintained at 50° C. and fed either downward or upward direction by gravity. Feeding upward reduces the number and size of bubbles trapped in the column. Crude DCPD is fed to the packed bed by $N_2$ pressure from a 5-gallon bomb placed on top of the column. Samples of feed and effluent are analyzed for delay time (induction time) and the exotherm generated, for every 30–45 minute to monitor the performance of adsorbents.

Alumina is selected for percolation. In order to minimize the amount of moisture adsorbed, alumina is dried in a 150°–200° C. oven before usage. Alumina beds are also run in series with a Linde 13X mole sieve column. Both mixing and percolation indicate that 13X mole sieve is more effective in reducing the delay time than alumina.

In order to achieve the delay time of 1 minute or less after adsorption, the delay time of feed is approximately 2-3 minutes.

The capacity or mileage (ratio of volume purified DCPD to adsorbent bed volume) of alumina depends on the impurity content of the DCPD feed. A mileage of about 80 is expected when DCPD is purified from the delay time of about 2 minutes to 1 minute or less.

A flow rate of 20 ml/min (0.24 gpm/ft$^3$ packing or residence time of approximately 15 minutes) is adequate. A residence time of less than about 10 minutes sharply increases the delay time of the column effluent. Longer contacting times than 15 minutes improve the purity of the effluent, especially when the DCPD feed has a high delay time or if some of packed alumina is exhausted.

At a constant throughput, the adsorption capacity is a function of the bed length. For various throughputs or flow rates with a constant bed length, slower flow rate gives higher adsorption capacity. At 20 ml/min flow rate, the estimated residence time is about 15 minutes (packing volume approximately 600 ml).

Preferably 13X molecular sieve is used as a finishing adsorbent by running alumina and 13X molecular sieve columns in series. The color of alumina is gradually darkened from the feed end as the bed gets old. Color developed in the column gives the column effluent a yellowish tint.

Calcination and Regeneration

Alumina is regenerated by purging with dry gas at 225° C. after drying applications. The adsorbent is regenerated to almost the initial activity by burning off the deposits at temperatures between 500°-600° C. However, applying temperature above 700° C. would adversely affect the activity.

Effects of regeneration temperature on the activity of alumina are shown by checking the delay time of DCPD treated with regenerated alumina at various temperatures. Spent alumina was placed in a temperature controlled oven (250°-650° C.) for one hour. Analyses of spent alumina and 13X mole sieve over temperature range of 300°-600° C. show that regeneration might be completed in 30-60 minutes. Organic residues in spent alumina do not burn off completely at 400° C. or below. Regeneration at 500°-600° C. changed dark shaded spent alumina back to the original white color.

Spent alumina regenerated at 500°-600° C. consistently outperforms fresh alumina dried at 150°-200° C. The findings led to investigation of the effects of calcining (drying at high temperature) on the activity of fresh alumina.

Fresh aluminas are calcined at 250°-650° C. and activities compared. The results show that the activities of calcined alumina gradually improve as the calcination temperature increases. The delay time of 10% topped 97% dicyclopentadiene is reduced from 2.0-2.5 minutes to 53 seconds after mixing with alumina dried at 250° C., but was further improved to below 35 seconds when the alumina was calcined at 650° C.

The activities of both calcined and regenerated alumina at 600°-650° C. are similar. The mileages of both calcined and once regenerated alumina at 600° C. are equivalent to fresh alumina dried at 150°-200° C.

When either the calcined or regenerated alumina is used as an adsorbent, purified dicyclopentadiene picks up greenish-yellow color. The colored material is concentrated in the pot of a laboratory batch distillation column when a colored effluent of the adsorption column is fractionated and purified dicyclopentadiene is removed from the overhead gradually. The results demonstrate that these colored compounds are high boiling impurities and are separated from purified dicyclopentadiene by distillation.

Distillation and Adsorption

The polymerization of distillation cuts indicates that 95% by weight dicyclopentadiene can be sufficiently purified by distillation for use in RIM. Distillation fractions of the lower purity dicyclopentadiene do not react well at normal catalyst levels, and the highest degree of polymerization achieved is a gel.

As shown in Table 2, the recovery of purified monomer is substantially improved by adsorption after distillation.

TABLE 2

|  | Yields, %[a] | |
|---|---|---|
|  | Distillation | Distillation/Adsorption |
| 97% DCPD | 80 | 90 |
| 95% DCPD | 40-65 | 80-85 |

[a]Assuming 1 minute or less delay time is acceptable for purified monomer. Calcined alumina is used as an adsorbent.

Spent alumina could be regenerated by heating to 500°-600° C. for 30 minutes. Performance of regenerated alumina appears to be equivalent to fresh alumina dried at 500°-600° C. The activity of fresh alumina could be substantially improved by calcinating at 500°-600° C.

Laboratory adsorption column tests showed that flow rates of 0.20-0.25 gpm/ft$^3$ packing, which give approximately 15 minutes residence time, are adequate. Slower flow rates would improve the efficiency, especially when much of the adsorbents are exhausted, but the improvements are minor.

Pure dicyclopentadiene (99.9+% by weight DCPD) is a crystalline solid having a melting point of 34° C. (90° F.) and a flash point of about 103° F. To be useful for spontaneous polymerization to form substantially crosslinked polymerized units of dicyclopentadiene, the polymerization mixture must be a liquid. To avoid a fire hazard the liquid polymerization mixture preferably has a flash point of 100° F. or higher. The most pure, commercially available, dicyclopentadiene is 97% dicyclopentadiene having a viscosity of about 3.5 centipoises (cps) and a flash point of about 80° F. A significant portion of the about 3% which is not DCPD is low boiling hydrocarbonaceous compounds, such as $C_1$ to $C_4$ alkane, alkene, aromatic and substituted aromatic compounds. These hydrocarbonaceous compounds are effective to prevent crystal formation. The viscosity is preferably raised by addition of elastomer as discussed herein. The flash point can be raised by addition of high boiling hydrocarbonaceous compounds, such as $C_5$-$C_{20}$ alkanes, alkenes and aromatic compounds.

Avoiding suppression of the flash point is also important. High boiling substituents may be used for the activator. Preferably, the alkyl groups of the alkyl aluminum activator have from 5 to 10 carbon atoms.

Monomer Character

The cycloolefin monomer preferably has a flash point of 100° F. or higher and a viscosity of from about 3 cps. to about 5 cps. with addition of materials such as elastomer which increase viscosity, the preferred range of viscosity is from bout 3 cps. to about 3000. For RIM, the more preferred viscosity range is from about 100 to about 1000 cps. Lower flash points make storage and handling expensive and complex due to fire prevention requirements.

In some in-mold polymerization processes, low viscosity monomer is advantageous, such as pour molding of detailed shapes. While in other polymerization processes, higher viscosity monomer is needed such as in reaction injection molding. High purity monomer is needed for fast polymerization of cycloolefin, such as dicyclopentadiene. However, at purities of about 99.8 and above, at 70° F. dicyclopentadiene is substantially nonfluid (i.e., a solid). At purities below 95 percent, the rate of polymerization is significantly reduced.

A preferred example of a a high flash point cycloolefin composition, includes a cycloolefin mixture. The cycloolefin mixture includes at least 80% by weight dicyclopentadiene. This composition has a flash point of greater than 100° F. and a viscosity of from about 3 cps to about 1000 cps at about 70° F. and about 1 atmosphere pressure. A preferred reactant solution is comprised of dicyclopentadiene; trialkylaluminum, where each alkyl contains from 5 to 10 carbon atoms where the trialkylaluminum is present in a dicyclopentadiene to trialkylaluminum molar ratio of about 80:1 to about 1300:1; and bis(2-methoxyethyl)ether, where the bis(2-methoxyethyl) ether is present in a trialkylaluminum to bis(2-methoxyethyl) ether molar ratio of at least 1:0.5.

A halogen-free reactant solution is comprised of dicyclopentadiene (hereinafter referred to as DCPD), trialkylaluminum and bis(2-methoxyethyl) ether. In the preferred embodiment of the reactant solution, dicyclopentadiene is the only monomer present. In other embodiments, the reactant solution may additionally contain up to about 20% of one or more other metathesis polymerizable, cycloolefin comonomers, so long as the comonomer does not lower the flash point of the reactant solution below 100° F. Representative cycloolefin comonomers include norbornene, norbornadiene, dimethanohexahydronaphthalene, and dimethanooctahydronaphthalene. The flash point of any particular combination of monomers is readily determinable without undue experimentation by employing the method of ASTM D3278.

The reactant solution also contains trialkylaluminum. Each alkyl is composed of from 5 to 10 carbon atoms and each alkyl can be straight chained or branched. The preferred trialkylaluminum is tri-n-octyl aluminum. The trialkylaluminum is present in a dicyclopentadiene to trialkylaluminum molar ratio of about 80:1 to about 1300:1, preferably about 200:1 to about 500:1.

The third component of the reactant solution is bis(2-methoxyethyl) ether. The molar ratio of the trialkylaluminum to bis(2-methoxyethyl) ether is at least about 1:0.5, preferably about 1:1 to about 1:4. For maximum effectiveness as a reactant solution in the method described in U.S. Pat. No. 4,400,340, the bis(2-methoxyethyl) ether is added to the monomer or combination of monomers before the trialkylaluminum is added.

In some embodiments, a preformed elastomer is added to the reactant solution. The addition of the elastomer serves to increase the viscosity of the reactant solution and improve the impact resistance of a final thermoset polymeric product produced in accordance with the method disclosed in U.S. Pat. No. 4,400,340. The elastomer is dissolved in an amount of from about 3 to about 15 weight percent, based on the weight of the monomer or combination of monomers. Illustrative elastomers include natural rubber, butyl rubber, polyisoprene, polybutadiene, polyisobutylene, ethylene-propylene copolymer, styrene-butadiene-styrene triblock rubber, random styrene-butadiene rubber, styrene-isoprene-styrene triblock rubber, and ethylene-propylenediene terpolymers.

Preferably, the high flash point dicyclopentadiene composition of the invention includes at least 50 percent by weight DCPD and more preferably 80 percent by weight dicyclopentadiene and has a flash point of greater than 100° F. Most preferably, the high flash point dicyclopentadiene composition of the invention includes at least 95 percent by weight dicyclopentadiene and has a flash point of more than 100° F.

The best mode now contemplated of carrying out this invention is exemplified by the following working examples of preferred specific embodiments. The invention is not limited to these specific examples.

EXAMPLES

Examples A–E illustrate preferred embodiments of reactant solutions comprised of DCPD, tri-n-octylaluminum (TNOCTAL) and bis(2-methoxyethyl)ether (diglyme).

Reactant solutions are made in the following manner: first, diglyme is added to dicyclopentadiene. Next, TNOCTAL is added to the diglyme-DCPD solution. The amount of each component is shown in Table A.

The flash point of each sample was actually measured by the method of ASTM D-3278 using a Seta flash closed tester (manufactured by Paul N. Gardner Co., Lauderdale by the Sea, Fla.). The flash point of each sample is shown in Table 2A.

TABLE 2A

|  | Example A | Example B | Example C | Example D | Example E |
|---|---|---|---|---|---|
| DCPD | 368 mmol | 379 mmol | 366 mmol | 368 mmol | 364 mmol |
| TNOCTAL | 1.1 mmol | 1.1 mmol | 1.3 mmol | 1.9 mmol | 4.7 mmol |
| diglyme | 4.4 mmol | 21 mmol | 1.3 mmol | 1.9 mmol | 4.7 mmol |
| Flash point | 102° F. | 105° F. | 104° F. | 105° F. | 105° F. |

Catalyst Preparation

The novel catalyst composition preferred for polymerization of cycloolefin preferably of norbornene-type monomers includes $WCl_4O$ and $WCl_6$ in a molar ratio of $WCl_4O$ to $WCl_6$ of from about 1:9 to 2:1 (i.e., about 10–67% $WOCl_4$) to about 90–33% $WCl_6$. A novel method of making the catalyst precursor material is provided, the major portion of which is $WCl_6$. The catalyst precursor is then contacted with controlled proportions of the oxygen donor. $WCl_6$ reacts with oxygen donor to form $WCl_4O$ in a molar ratio of $WCl_4O$ to $WCl_6$ of between about 1:9 and 2:1.

The percentage increase of catalyst activity as determined by the decrease in the amount of catalyst needed to successfully polymerize monomer to a residual monomer level of 1% or less is from 100%–1000%. The polymerized cycloolefin products of the present invention have residual monomer of less than 2 percent. Preferably these products have less than 1.0 percent residual monomer. More preferably the polymer products of the invention contain less than 0.8 percent residual monomer. Most preferably, the polymerized polyolefin products of the invention contain less than 0.5 percent residual monomer. As the proportion of residual monomer decreases, the properties of the product improve. For example, the flexural modulus increases and latent odor decreases to be lower than perceptible by smell for most human beings at amounts less than 1 percent. Preferably, the catalyst composition is from about 10 to 75% $WCl_4O$ and is from about 25 to 90 percent $WCl_6$. Most preferably the catalyst composition is from about 25 to 50 percent $WCl_4O$ and from 50 to 75 percent $WCl_6$. The method provides controlled oxygen addition through reaction with a limited proportion of oxygen supplied by a source of oxygen, such as a hydrated salt, water, wet molecular sieves, or an alcohol. For example, $WCl_6$ is rapidly converted to $WOCl_4$ by treatment with a number of oxygen-containing materials, including $H_2O$, alkyl alcohols, $Cl_3CNO_2$ and $CH_3OSi(CH_3)_3$. A preferred alkyl alcohol is t-butanol.

In a preferred embodiment a gaseous mixture of carrier gas such as nitrogen and water vapor is added to a stirred mixture of catalyst precursor (for example $WCl_6$) in solvent such as toluene under an inert atmosphere. The gaseous mixture of carrier gas and water vapor is carried to a point beneath or slightly above the solvent surface in the mixing vessel from a container of the solvent and water into which is introduced dry carrier gas. By proportioning the amount of water to the amount of catalyst precursor, oxygen addition from the water to the catalyst precursor to form the product is controlled. The amount of water initially in the feed container is in proportion to the amount of catalyst precursor in the mixing vessel. The generalized reaction I is believed to take place as follows:

$H_2O + WCl_6 \rightarrow WOCl_4 + 2HCl$ (I);

The molar ratio of water to catalyst precursor is preferably from 0.25 to 0.75. The inactivation of catalyst product may occur if overexposure to oxygen-donor material is permitted. Oxidation products which are inactive for cycloolefin polymerization are $WO_2Cl_2$ and $WO_3$. The reaction is complicated by the fact that $WOCl_4$, while more stable than $WCl_6$, is still susceptible to hydrolysis as shown in reactions II:

| (II) | $WCl_6 + H_2O$ | $WOCl_4 + 2HCl$ |
| --- | --- | --- |
| | $WOCl_4 + H_2O$ | $WO_2Cl_2 + 2HCl$ |
| | $WO_2Cl_2 + H_2O$ | $WO_3 + 2HCl$ |

Therefore, it is necessary to carefully control the reaction to minimize the formation of these byproducts.

$WCl_4O$ catalyst is prepared by controlled addition of water. This is readily accomplished either by sparging a $WCl_6$ solution with wet $N_2$ gas or by adding a hydrated inorganic salt, such as $FeSO_4 \cdot 7H_2O$. The preferred proportion of water is about 0.5 mole per mole tungsten. Phenol and acetylacetone (acac) are added to solubilize and stabilize respectively the system in cycloolefin. Catalyst prepared in this fashion is effective in polymerization of cycloolefins such as DCPD at a cycloolefin to catalyst ratio of as low as 14000:1.

Alcohols such as methanol and isopropanol and $CH_3OSi(CH_3)_3$ give slight improvements in catalyst activity. This may be due to formation of byproducts. In the controlled hydrolysis of $WCl_6$ wet nitrogen gas is sparged through a 0.1M toluene solution of $WCl_6$ until a known amount of water is added. The appropriate volume of water is premixed with toluene so that the gas is also saturated with toluene vapor. During the addition, a small amount of the precipitate forms and the blue-purple solution gains a very faint reddish tint. After the addition of water is complete, one equivalent each of phenol and acetylacetone (acac) are added to give the catalyst.

The second embodiment of the catalyst preparation method uses hydrated inorganic salts as water carriers. $FeSO_4 \cdot 7H_2O$ is crushed to a powder. The $WCl_6$ solution is then added and the mixture is allowed to stir for an hour. The solution is then decanted away from the salt. Phenol and acetylacetone (acac) are added as above.

In a alternative preparation of catalyst, very pure $WCl_6$ is treated with tert-butanol. Tert-butanol dissociates to form water and iso-butylene. Thus, t-butanol serves as a water source in the same way that hydrated salts or molecular sieves might. Addition of t-butanol to a suspension of $WCl_6$ in an organic solvent such as toluene or xylene greatly increases the activity of the catalyst. In order to prepare catalyst suitable for RIM processing, nonylphenol and acac are added as disclosed in U.S. Pat. No. 4,400,340. The molar ratio of t-butanol to tungsten is preferably from 0.10 to 0.75, most preferably from 0.25 to 0.50.

Unlike the case of water vapor, where the oxygen source can be added to the catalyst before or after addition of the phenol, with t-butanol it is preferred to add t-butanol before the phenol.

A preferred polymerization catalyst composition includes a mixture of a compound of the general formula:

$WCl_mO_n$ and

wherein R is an alkyl group having 3 to 20 carbon atoms; m is 4 or 6 and n is 1 or 0. The polymerization catalyst preferably further includes a compound of the general formula:

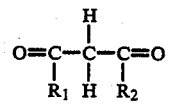

wherein $R_1$ and $R_2$ are independently hydrogen or an alkyl group of from 1 to 5 carbons. In compositions more preferred n is 1; m is 4 and R is nonyl. Most preferably the polymerization catalyst composition further includes compound selected from the group consisting of of 2,4-pentanedione and diglyme. A most preferred polymerization catalyst composition is a compound of the general formula

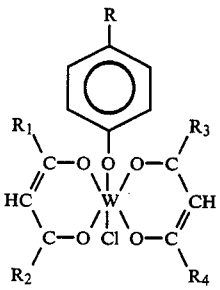

wherein R is an alkyl group of from 1 to 20 carbon atoms; R₁ is hydrogen or an alkyl group of from 1 to 5 carbon atoms; R₂ is hydrogen or an alkyl group of from 1 to 5 carbon atoms; R₃ is hydrogen or an alkyl group of from 1 to 5 carbon atoms; R₄ is hydrogen or an alkyl group of from 1 to 5 carbon atoms.

Noncycloolefin Solvent-Free Catalyst Solution

A catalyst solution of WCl₆ and WCl₄O in a 1:1 molar ratio in phenol and acac is preferred as described above. The catalyst solution of WCl₆ and WCl₄O in toluene is added to the DCPD and warmed at 35° C. for 24 hours to vaporize the toluene. The resulting solution is substantially free of toluene and other noncycloolefin solvents for the WCl₆—WCl₄O catalyst. That is, other than cycloolefins there is substantially no solvent present.

One of the advantages of the reaction injection molding (RIM) process is that since the reactive streams are initially low viscosity liquids it should be especially suited for molding large or intricately shaped parts. The prior art however does not teach any method to control or prevent the occurrence of gellation prior to the substantially complete conversion of monomer into polymer. Gellation of the monomer is characterized by a sharp increase in the viscosity of the monomer, generally to greater than 100,000 centipoise, at some time prior to the substantially complete conversion of monomer into polymer.

Two Part Activator Embodiment

An improved method of the invention is for making a thermoset polymer of cyclic olefins, for example, dicyclopentadiene. Dicyclopentadiene monomer is polymerized with a three component olefin metathesis catalyst system whereby the length of the gel time relative to the cure time can be controlled by the proportions of the catalyst system components. In this way, the gel time is made to coincide with the cure time without affecting any of the other properties of the polymer. The catalyst system is made up of a two part activator and a catalyst which is a monomer soluble or solvent soluble tungsten compound. The two part activator includes a trialkylaluminum compound or a dialkylaluminum chloride, as the first part of the activator, and a dialkylaluminum iodide as the second part of the activator. In a preferred embodiment, the three parts of the olefin metathesis catalyst, plus the monomer, form the basis of at least two separate reactive streams. These can be mixed in one place, such as the mixing head of a reaction injection molding machine, and then injected into a mold where they will set up into a solid insoluble cross-linked polymer. By varying the ratio of the activator to catalyst, the gel time, as a fraction of the total cure time, can be varied from approximately 35% of the cure time to 100% of the cure time. To so vary the gel time the ratio of activator to catalyst is varied from 3:1 to 2.4:1 on a molar basis.

U.S. Pat. No. 4,458,037 (Leach 1) incorporated herein by reference discloses an improved process for making a cellular crosslinked polymerized dicyclopentadiene with an olefin metathesis catalyst system. An improvement of the Leach process is the use of dialkylaluminum iodides such as diethylaluminum iodide as catalyst activators. (The use of a two component olefin metathesis catalyst consisting of a tungsten oxyhalide or halide such as tungsten hexachloride and a dialkylaluminum iodide for the polymerization of dicyclopentadiene results in a polymerization which does not exhibit gellation due to crosslinking, prior to the exothermic polymerization and thus can be expanded to a uniform cellular polymer.) The use of other aluminum alkyls such as trialkylaluminums or dialkylaluminum chlorides is found to be unsatisfactory for foam formation and mold filling. Their use with a tungsten catalyst such as tungsten hexachloride results in the early formation of a gelled crosslinked network. Such networks in general cannot be expanded uniformly.

In a preferred embodiment composition and method of making a cellular crosslinked polymerized dicyclopentadiene provides dicyclopentadiene (DCPD) monomer which is polymerized with an olefin metathesis catalyst system discussed above, this improved process provides uniform cellular polymers of cyclic olefins such as dicyclopentadiene, these polymers have a substantially crosslinked structure and improved physical properties. In a preferred embodiment, the three part olefin metathesis catalyst (catalyst and two part activator), and the monomer and a blowing agent form the basis of at least two separate reactant streams. These reactant streams can be mixed in one place, such as the mixing chamber of a reaction injection molding machine, and then injected into another place such as a mold, where the monomer polymerizes to a cellular crosslinked polymer. The addition of a surfactant or foam stabilizing agent to the monomer mixture results in the formation of a cellular polymer where the bubbles are much smaller and of a more uniform size. Also a higher percentage of the bubbles in the cellular polymer are closed when a surfactant has been added.

By deleting the blowing agent intricate molds are readily filled using the combined reactant streams. The resulting product is an intricately shaped noncellular polymer. Molding may be by pour molding, spray molding, RIM, etc.

The polymerization of the dicyclopentadiene monomer is preferably catalyzed by the three part metathesis catalyst system. Catalyst is dissolved in one reactive stream while the two part activator is added to a second monomer stream.

Use of a three component olefin metathesis catalyst as described above containing a trialkylaluminum compound or a dialkylaluminum chloride and only a small amount of dialkylaluminum iodide relative to either of the other two components results in a polymerization which also does not exhibit gellation due to crosslinking and thus can be used to produce uniform cellular polymers. In addition, polymers produced by this process form a more highly crosslinked structure after their expansion to a cellular polymer than the polymers of the invention of U.S. Pat. No. 4,458,037 (Leach 1), and thus have more desirable end properties such as creep resistance and compressive strength. Low density foams can be made using the composition and method of the present invention.

The first part of the activator is composed of a trialkylaluminum compound or dialkylaluminum chloride where each alkyl group contains from one to twelve carbon atoms. Preferred dialkylaluminum chlorides are diethyl aluminum chloride and dioctylaluminum chloride. A preferred trialkylaluminum compound is trioctylaluminum.

The second part of the activator is composed of a dialkylaluminum diodide where each alkyl group contains from one to twelve carbon atoms. Preferred dialkylaluminum iodides include diethylaluminum iodide and dioctylaluminum iodide. Dioctylaluminum iodide is preferred.

Blowing Agent

A blowing agent is incorporated into the reactive streams in order that a product having a cellular structure is formed during polymerization. Any of the conventional blowing agents used in reaction injection molding processes or related processes may be employed provided that the blowing agent does not poison or otherwise adversely affect the metathesis catalyst. Preferred blowing agents include low boiling organic compounds, i.e. compounds which are liquids under ambient conditions but which are volatilized under polymerization conditions, and inert gasses. Representative low boiling organic compounds include hydrocarbons such as pentane and hexane, and halogenated hydrocarbons such as methylene chloride, trichlorofluoromethane and 1,1,2-trichloro-1,2,2-trifluoroethane. Representative inert gasses include nitrogen, argon and fluorinated hydrocarbons, such as dichlorodifluoromethane and 1,2-dichloro-1,1,2,2-tetrafluoroethane.

The blowing agent is incorporated into either or both reactive streams, or it may be added to a separate monomer stream. The amount of blowing agent to be incorporated is from about 2 to about 30, preferably from about 4 to about 20, percent by weight based on the weight of the monomer. The greater the amount of blowing agent used the less dense the final cellular crosslinked polymer produced.

In some embodiments, the cellular crosslinked polymer of this invention is made and molded by RIM or related processes.

The two parts of the metathesis-catalyst system are separately mixed with monomer and blowing agent to form two suitable solutions which are placed in separate vessels. These vessels provide the source for separate streams. The two streams are combined in one place, such as a RIM machine's mixing head, and then injected into a second place, such as a mold where polymerization takes place.

The invention is not intended to be limited to embodiments employing two streams each containing monomer and blowing agent. It will be obvious to one skilled in the art that there may be situations where it is desirable to have monomer incorporated in just one stream or to employ a plurality of streams where the additional streams contain monomer or additives or both.

Bubble Stabilization

In some embodiments, a foam stabilizing agent such as a surfactant is added to make the bubbles smaller and more uniform in size. This generally also results in the formation of foams in which a higher percentage of the cells are closed than in embodiments which do not contain a foam stabilizing agent. Having the bubbles small and of uniform size generally results in improved properties such as flex modulus, impact resistance and compressive strength for the foam. Having a higher amount of closed cells is generally preferred for a number of applications such as insulation.

The use of surfactants as foam stabilizers is well known in the preparation of polyurethane foams to produce foams with well dispersed small bubbles of uniform size. Surfactants commonly used for polyurethanes are composed of graft or block copolymers of polysilicones and polyethers such as polypropylene oxide or polyethylene oxide. Examples of such surfactants include silicone surfactants such as L-5410, L5420, L-5430, L540, and L-5350 manufactured by Union Carbide Corporation. However, with polydicyclopentadiene, surfactants such as these are ineffective. Other common surfactants such as glyceryl dioleate, polyoxyethylated tert-octylphenol, polyethyleneglycol 300 dilaurate, sodium n-octyl-sulfate, alkyltrimethylammonium salts, polysorbates, alkanolamides, and perfluoroalkylpolyethers are also ineffective.

Surfactants that are effective are fluorinated alkyl methacrylate copolymers. Examples of suitable commercially available surfactants include FC-740 and FC-432, which are fluorinated alkyl methacrylate copolymer surfactants sold by Minnesota Mining and Manufacturing Company. Other similar surfactants composed of fluorinated copolymers of alkyl methacrylates are also effective. The molecular weight of the polymeric surfactant appears not to have an effect on its foam stabilizing ability so that the only limit on molecular weight would be that it not be so high as to require large amounts of inert solvent as a diluent to make it easy to transfer, weight, or otherwise handle the surfactant solution. In addition, the solvent that the surfactant is dissolved in should not interfere with or inhibit the polymerization. The amount of surfactant added should be from about 0.1% to about 1.0% of the amount of dicyclopentadiene monomer. The surfactant may be added to either the catalyst and monomer stream or the activator and monomer stream. Since the surfactant causes the monomer streams to foam under agitation, and thus have a lower density, it is preferably added to both streams so that they will have the same density.

In some embodiments, a nucleating agent, such as calcium carbonate, is added to at least one of the reactant streams. The nucleating agent affects the structure of the foam by making the cells small and uniform. Other suitable nucleating agents include talc, magnesium carbonate, barium carbonate, zinc carbonate, lead carbonate, magnesium oxide, calcium oxide, polyethylene, and silica. The preferred nucleating agent is silica.

EXAMPLES 1 AND 2

In Example 1 a 0.1M solution of a tungsten containing catalyst solution is prepared by adding 20 grams of $WCl_6$ in 60 ml of dry toluene under a $N_2$ atmosphere and then adding a solution of 8.2 grams of p-tert-butyl phenol in 30 ml of toluene. The catalyst solution is sparged overnight with nitrogen to remove the HCl generated by the reaction of $WCl_6$ with the p-tert-butylphenol. In this and in all the following examples, phenol is used as a shorthand for p-tert-butylphenol and for simplicity the solution is referred to as $WCl_6$/phenol. Then a 0.033M catalyst/monomer solution is prepared by mixing under nitrogen 10 ml of dicyclopentadiene, 0.07 ml of benzonitrile and 5 ml of the 0.1M catalyst solution. An activator/monomer solution is prepared by combining, under nitrogen, 8.6 ml of dicyclopentadiene, 0.1 ml of isopropyl ether and 0.36 ml of 1.0M diethylaluminum chloride ($Et_2AlCl$) in DCPD.

Polymerization is accomplished by adding 1.1 ml of the 0.033M catalyst/monomer solution to 8.9 ml of the activator/monomer solution. Both solutions are initially at 25° C. They are vigorously mixed. After a brief induction period a sharp exotherm is observed. A solid, insoluble polymer is formed. The time that elapses until rapid polymerization begins and the total exotherm of the sample above the starting temperature are shown in Table I.

In Example 2 the above procedure is repeated except that 0.36 ml of 1.0M $EtAlCl_2$ is used in place of $Et_2AlCl$ to prepare the activator solution and the reaction is started at 40° C. A solid, insoluble polymer is formed. The results are shown in Table 3.

TABLE 3

|  | Example 1 | Example 2 |
|---|---|---|
| DCPD | 72 mmol | 72 mmol |
| $WCl_6$/Phenol | 0.036 mmol | 0.036 mmol |
| $Et_2AlCl$ | 0.36 mmol | — |
| $EtAlCl_2$ | — | 0.36 mmol |
| Benzonitrile | 0.04 mmol | 0.04 mmol |
| Isopropyl Ether | 0.72 mmol | 0.72 mmol |
| Initial Temperature | 25° C. | 40° C. |
| Time Until Exotherm | 15 sec. | 445 sec. |
| Exotherm | 122° C. | 147° C. |

EXAMPLES 3–8

In Examples 3 through 8 the procedure described in Example 1 is repeated except that different moderators are added to the activator/monomer solution. In each example the ratio of moles of moderator to moles of $Et_2AlCl$ is held constant at 2:1. In Example 3, di-n-butyl ether is added while in Example 4, diisopropyl ether is used. In Example 5, ethyl benzoate is used while in Example 6, phenylethyl acetate is added. In Example 7, diisopropyl ketone is added. Lastly, in Example 8, tetrahydrofuran is added. In each example, the initial temperature is 25° C. (+1° C.). Example 8 is the only case where a solid insoluble polymer is not obtained. The results are listed in Table 4.

TABLE 4

|  | Example 3 | Example 4 | Example 5 | Example 6 | Example 7 | Example 8 |
|---|---|---|---|---|---|---|
| DCPD | 72 mmol | 72 mmol | 72 mmol | 72 mmol | 72 mmol | 72 mmol |
| $WCl_6$/Phenol | 0.036 mmol | 0.036 mmol | 0.036 mmol | 0.036 mmol | 0.036 mmol | 0.036 mmol |
| $Et_2AlCl$ | 0.36 mmol | 0.36 mmol | 0.36 mmol | 0.36 mmol | 0.36 mmol | 0.36 mmol |
| Di-n-butyl ether | 0.72 mmol | — | — | — | — | — |
| Diisopropyl ether | — | 0.72 mmol | — | — | — | — |
| Ethyl benzoate | — | — | 0.72 mmol | — | — | — |
| Phenyl ethyl acetate | — | — | — | 0.72 mmol | — | — |
| Diisopropyl ketone | — | — | — | — | 0.72 mmol | — |
| Tetrahydrofuran | — | — | — | — | — | 0.72 mmol |
| Benzonitrile | 0.04 mmol | 0.04 mmol | 0.04 mmol | 0.04 mmol | 0.04 mmol | 0.04 mmol |
| Time until Exotherm | 42 sec. | 15 sec. | 60 sec. | 282 sec. | 160 sec. | no rxn. |
| Exotherm | 153° C. | 122° C. | 155° C. | 157° C. | 147° C. | — |

EXAMPLES 9–12

In Examples 9 through 12 the activator to catalyst ratios are varied. In Example 9, 0.88 ml of catalyst/monomer solution, described in Example 1 is added to 7.1 ml of DCPD containing sufficient $Et_2AlCl$ and di-n-butyl ether to give the composition listed in Table 5. In Example 10, 0.44 ml of the same catalyst/monomer solution as used in Example 9 is added to 7.5 ml of the same activator/monomer solution used in Example 9, to give the final composition listed in Table 5. In Example 11, 4.0 ml of a catalyst/monomer solution prepared by mixing 20 ml of DCPD with 1.5 ml of a 0.1M $WCl_6$/phenol solution, is mixed with 4.0 ml of an activator/monomer solution. In this activator solution there is sufficient $Et_2AlCl$ to give a DCPD to alkylaluminum ratio of 100:1 and sufficient di-n-butyl ether to give a di-n-butyl ether to aluminum ratio of 2:1. In Example 12, 4.0 ml of the catalyst/monomer solution used in Example 11 is mixed with 2.0 ml of DCPD and 2.0 ml of the activator/monomer solution used in Example 11. In each case a solid, insoluble polymer is formed. The results of these reactions showing a variation in the exotherms due to variations in the Al/W ratio, are listed in Table 5.

TABLE 5

|  | Example 9 | Example 10 | Example 11 | Example 12 |
|---|---|---|---|---|
| DCPD | 57.6 mmol | 57.6 mmol | 57.6 mmol | 57.6 mmol |
| $WCl_6$/Phenol | 0.029 mmol | 0.0145 mmol | 0.029 mmol | 0.029 mmol |
| $Et_2AlCl$ | 0.29 mmol | 0.29 mmol | 0.29 mmol | 0.145 mmol |
| Di-n-butyl ether | 0.58 mmol | 0.58 mmol | 0.58 mmol | 0.29 mmol |
| Benzonitrile | 0.033 mmol | 0.016 mmol | 0.033 mmol | 0.033 mmol |
| DCPD/Al | 200 | 200 | 200 | 400 |
| DCPD/W | 2000 | 4000 | 2000 | 2000 |
| Al/W | 10/1 | 20/1 | 10/1 | 5/1 |
| Time to Exotherm | 50 sec. | 48 sec. | 33 sec. | 43 sec. |
| Exotherm | 153° C. | 120° C. | 145° C. | 168° C. |
| Percentage Residual DCPD in polymer product | 3.0 | 4.7 | 3.0 | 1.5 |

EXAMPLES 13–15

In Examples 14–15 a small amount of a polar material is added to the catalyst/monomer solution in order to illustrate the effect of polar material on shelf-life. In Example 13, a catalyst/monomer solution is prepared by adding 2.0 ml of a 0.1M tungsten containing catalyst solution, as described in Example 1, to 20 ml of DCPD in a nitrogen purged tube. This mixture gelled to a non-flowing material within 24 hours. In Example 14, the same procedure is carried out except that 0.03 ml of benzonitrile is added, giving a final benzonitrile to tungsten halide ratio of 1.5:1. This mixture does not gel and is catalytically active after 4 weeks. Example 15 illustrates the result when tetrahydrofuran is added to give a tetrahydrofuran to tungsten halide ratio of 1.5:1.

Again, a greatly improved storage stability is observed. The results are listed in Table 6.

TABLE 6

|  | Example 13 | Example 14 | Example 15 |
|---|---|---|---|
| DCPD | 130 mmol | 130 mmol | 130 mmol |
| $WCl_6$/Phenol | 0.2 mmol | 0.2 mmol | 0.2 mmol |
| Benzonitrile | — | 0.3 mmol | — |
| Tetrahydrofuran | — | — | 0.3 mmol |
| Condition after 24 hours | gelled | low viscosity | low viscosity |
| Condition after 4 weeks | gelled | low viscosity | low viscosity |
| Activity after 4 weeks | gelled | acceptable | acceptable |

EXAMPLES 16–18

In Examples 16–18, the concentration of di-n-butyl ether incorporated into the activator/monomer solution to serve as a moderator is varied. In Example 16, the procedure used in Example 1, is followed with the exception that 0.078 ml of n-butyl ether is substituted for the diisopropyl ether. This gives a final ratio of di-n-butyl ether to alkylaluminum of 1.5:1. In Example 17, the procedure is repeated except that 0.156 ml of di-n-butyl ether is added, giving a final ether/Al ratio of 3:1. In Example 18, sufficient di-n-butyl ether is added to bring the final ether to alkylaluminum ratio to 5:1. All the reactions in Table 5 are initiated at 25° C. In each case a solid, insoluble polymer is formed. The results of the reactions are listed in Table 7.

TABLE 7

|  | Example 16 | Example 17 | Example 18 |
|---|---|---|---|
| DCPD | 57.6 mmol | 57.6 mmol | 57.6 mmol |
| $WCl_6$/Phenol | 0.029 mmol | 0.029 mmol | 0.029 mmol |
| $Et_2AlCl$ | 0.29 mmol | 0.29 mmol | 0.29 mmol |
| Di-n-butyl ether | 0.43 mmol | 0.86 mmol | 1.45 mmol |
| Benzonitrile | 0.033 mmol | 0.033 mmol | 0.033 mmol |
| Ether/Al | 1.5 | 3.0 | 5.0 |
| Elapsed time until exotherm | 36 sec. | 55 sec. | 75 sec. |
| Exotherm | 150° C. | 158° C. | 159° C. |

EXAMPLES 19–21

In Examples 19–21, the level of $Et_2AlCl$ used in the polymerization of DCPD are varied. In Example 19, 18.5 ml of DCPD was mixed under $N_2$ with 1.5 ml of a 1.0M solution of $Et_2AlCl$ in DCPD and with 0.55 ml of di-n-butyl ether. Then in a $N_2$ purged tube 8.9 ml of this activator/monomer solution is mixed with 1.1 ml of a catalyst/monomer solution as described in Example 1. In Example 20, 4.5 ml of the activator/monomer solution used in Example 19 is combined with 4.4 ml of DCPD and 1.1 ml of the catalyst/monomer solution used in Example 20. In Example 21, 2.5 ml of the activator/monomer solution used in Example 19 is combined under $N_2$ with 6.4 ml of DCPD and 1.1 ml of the catalyst/monomer solution used in Example 19. The final compositions of these reaction mixtures are listed in Table 8. All reactions are initiated at 25° C.

TABLE 8

|  | Example 19 | Example 20 | Example 21 |
|---|---|---|---|
| DCPD | 72 mmol | 72 mmol | 72 mmol |
| $WCl_6$/Phenol | 0.036 mmol | 0.036 mmol | 0.036 mmol |
| $Et_2AlCl$ | 0.72 mmol | 0.36 mmol | 0.20 mmol |
| Di-n-butyl ether | 1.44 mmol | 0.72 mmol | 0.40 mmol |
| Benzonitrile | 0.04 mmol | 0.04 mmol | 0.04 mmol |
| DCPD/Al | 100 | 200 | 360 |

TABLE 8-continued

|  | Example 19 | Example 20 | Example 21 |
|---|---|---|---|
| Di-n-butyl ether/Al | 2/1 | 2/1 | 2/1 |
| Elapsed time until exotherm | 40 sec. | 55 sec. | 144 sec. |
| Exotherm | 150° C. | 151° C. | 145° C. |

EXAMPLES 22–25

The effect of impurities on the catalyst system is illustrated in Examples 22 through 25. In Example 22, a 0.007M solution of $WCl_6$/phenol in DCPD is prepared by mixing under nitrogen 150 ml of DCPD with 10.8 ml of a 0.1M $WCl_6$/phenol solution in toluene and 0.11 ml of benzonitrile. Then 3.0 ml of this solution is mixed under nitrogen with 3 ml of a DCPD solution containing $AlEt_2Cl$ at a level DCPD to alkylaluminum of 150:1 and di-n-butyl ether at a level of ether to alkylaluminum of 1.5:1.

In Example 23, a 10 ml sample of the catalyst/monomer solution used in Example 22 is mixed with an impurity, 0.036 mmol of $H_2O$, added as a dispersion in DCPD. One and one-half hours later, 3 ml of this mixture is mixed under nitrogen with 3.01 of the activator/monomer solution described in Example 22. The reaction is repeated this time combining the activator/monomer solution with the catalyst/monomer solution 18 hours after the $H_2O$ had been added.

Example 24 is done in the same manner as Example 23 with the exception that 0.036 mmol of tert-butyl hydroperoxide is added to a second 10 ml sample of the catalyst solution rather than $H_2O$. The reactivity of the resultant mixture is checked 1½ and 18 hours after the addition of the impurity. Example 25 is carried out in the same manner with the exception that 0.072 mmol of di-tert-butylperoxide is the impurity added initially to 10 ml sample of the catalyst/monomer solution. In every case a solid, insoluble polymer is formed.

TABLE 9

|  | Example 22 | Example 23 | Example 24 | Example 25 |
|---|---|---|---|---|
| DCPD | 43 mmol | 43 mmol | 43 mmol | 43 mmol |
| $WCl_6$/Phenol | 0.021 mmol | 0.021 mmol | 0.021 mmol | 0.021 mmol |
| $H_2O$ | — | 0.01 mmol | — | — |
| tert-butyl-hydroperoxide | — | — | 0.01 mmol | — |
| Di-tert-butyl-peroxide | — | — | — | 0.02 mmol |
| $Et_2AlCl$ | 0.14 mmol | 0.14 mmol | 0.14 mmol | 0.14 mmol |
| Added Impurity/W | 0 | 0.5/1 | 0.5/1 | 1/1 |
| Induction Time after 1½ hrs. | 31 sec. | 50 sec. | 98 sec. | 33 sec. |
| Exotherm after 1½ hrs. | 173° C. | 171° C. | 168° C. | 171° C. |
| Induction time after 24 hrs. | 36 sec. | 98 sec. | 266 sec. | 73 sec. |
| Exotherm after 24 hrs. | 170° C. | 170° C. | 155° C. | 169° C. |

EXAMPLES 26–33

In each of Examples 26–33, polymerized dicyclopentadiene is made by RIM processing using a standard RIM machine. The following description illustrates the procedure for molding. First the desired amount of catalyst mixture and activator dicyclopentadiene is charged to two 2 gallon tanks. The tanks are located on different sides of the RIM machine: the tank on the A side is the one to which the activator mixture is added and the tank on the B side is the one to which the catalyst solution is added. If desired, rubber and/or organic resins are added as a predissolved solution in dicyclopentadiene. Also solid fillers are added, if desired.

The tanks are then closed off and placed under a nitrogen atmosphere. Sufficient $Et_2AlCl$ is in the activator solution feed tank (the A tank) to bring the alkylaluminum concentration to 0.048M and sufficient di-n-butyl ether present to achieve an ether to alkylaluminum ratio of 1.5:1. Sufficient $WCl_6$/phenol to bring the concentration of the catalyst in the catalyst side (B side) to 0.007M is present in the catalyst solution feed tank (B tank). The catalyst solution is prepared as a 0.1M solution in toluene. All transfers are done in a way to preclude the entrance of oxygen or moisture into the system. The solution are continuously thoroughly blended in their respective tanks.

The mixing of the activator solution (A stream) and the catalyst solution (B stream) is accomplished using a standard impingement type RIM mixhead. The ratio of the activator/monomer solution mixed with catalyst/monomer solution is 1:1. The impingement mixing is accomplished by passing both the solutions through orifices 0.032" in diameter at a flow rate approximately 80 ml/sec. This required pumping pressure of approximately 1000 psi.

The resulting mixture flows directly into a mold heated between 50° C. and 60° C. The mold is made out of aluminum and is chrome plated. The mold has a flat cavity which forms a plaque sample $10'' \times 10'' \times \frac{1}{8}''$ thick. A clamping force of 1.5 tons is used to keep the mold closed. The finished samples are removed at various times after mold filling ends.

In Example 26, the outlined molding procedure is followed where there is added 10 wt% added styrene-butadiene-styrene rubber (Kraton no. 1102 manufactured by Shell Chemical Co). The sample is removed from the mold after 2 minutes. In Example 27 a material of the same composition as Example 26 is produced. This time the mold is opened 30 seconds after the combined streams are injected. The surface features of Example 27 are noticably better than those of Example 26. In Example 28, 10 wt% of a thermally polymerized dicyclopentadiene resin is added in addition to both the catalyst/monomer and the activator/monomer solutions in addition to the styrene-butadiene-styrene rubber.

Various inorganic fillers are incorporated into the dicyclopentadiene polymer by adding equal amounts to both the catalyst/monomer and the activator/monomer solutions. In Example 29, samples are made containing 33 wt% $\frac{1}{8}''$ milled glass (P117B grade of Owens Corning Co.). These samples are made by initially slurrying the glass into both solutions of the catalyst/monomer and the activator/monomer. Otherwise, these solutions are identical to those used in Example 28. In Example 30 a composition consisting of 10 wt% wollastonite is made by adding the filler to a formulation identical to that described in Example 28. In Example 31 the same procedure is followed as in Example 30 except that a 33 wt% level of wollastonite is employed. In Example 32, 25 wt% wollastonite is added to the formulation described in Example 27. In each case a solid, insoluble polymer is formed. Representative properties of Examples 26-32 are listed in Tables 10 and 10A.

Example 33 is a RIM processed poly(DCPD) made without any rubber additives.

TABLE 10

|  | Example 26 | Example 27 | Example 28 | Example 29 |
|---|---|---|---|---|
| Resin Composition |  |  |  |  |
| % cyclopentadiene resin | — | — | 10 | 10 |
| % Kraton 1102 | 10 | 10 | 10 | 10 |
| % DCPD | 90 | 90 | 80 | 80 |
| Filler Composition |  |  |  |  |
| wt % $\frac{1}{8}''$ milled glass | — | — | — | 33 |
| wt % wollastonile | — | — | — | — |
| Tensile Properties |  |  |  |  |
| Strength (psi) | — | 4,860 | 5,230 | — |
| Modulus (psi) | — | 262,000 | 257,000 | — |
| Elongation at yield (%) | — | 4.0 | 4.0 | — |
| Flexural Properties |  |  |  |  |
| Strength (psi) | 7,400 | 8,600 | — | 8,200 |
| Modulus (psi) | 235,000 | 250,000 | — | 526,000[2] |
| Impact Properties |  |  |  |  |
| Notched Izod (ft #/in. notch) | 13.2 | 10.5 | 11.0 | 2.7 |
| Plate Impact at 5000"/min. (ft. #) |  |  |  |  |
| 23° C. | 21.0 | — | — | — |
| 0° C. | 15.7 | — | — | — |
| −20° C. | 12.3 | — | — | — |
| Heat Deflection Temperature at 264 psi (°C.) | — | 65° | 64° | 81° |
| Coefficient of Thermal Expansion (in/in °F.)[2] | — | $6.0 \times 10^{-5}$ | — | $3.2 \times 10^{-5}$ |
| Linear Mold Shrinkage[2] (%) | 2.6 | 3.5 | 3.1 | 1.0 |
| Percentage Residual Monomer | 3.0 | 3.0 | 3.0 | 0.03 |

[1]Value in the direction parallel to the direction of flow.
[2]Value is the average of the values obtained perpendicular to the direction of flow and parallel to the direction of flow.

TABLE 10A

|  | Example 30 | Example 31 | Example 32 | Example 33 |
|---|---|---|---|---|
| Resin Composition | | | | |
| % cyclopentadiene resin | 10 | 10 | — | — |
| % Kraton 1102 | 10 | 10 | 10 | — |
| % DCPD | 80 | 80 | 90 | 100 |
| Filler Composition | | | | |
| wt % 1/8" milled glass | — | — | — | — |
| wt % wollastonile | 10 | 33 | 25 | — |
| Tensile Properties | | | | |
| Strength (psi) | 4,700 | — | 4,290 | 5,050 |
| Modulus (psi) | 426,000[1] | — | 683,000[1] | 270,000 |
| Elongation at yield (%) | 3.0 | — | 2.0 | 3.4 |
| Flexural Properties | | | | |
| Strength (psi) | 9,000 | 8,400 | 8,300 | 8,400 |
| Modulus (psi) | 390,000[2] | 670,000[2] | 480,000[2] | 270,000 |
| Impact Properties | | | | |
| Notched Izod (ft #/in. notch) | 2.0 | 2.9 | — | 2.3 |
| Plate Impact at 5000"/min. (ft. #) | | | | |
| 23° C. | 11.2 | — | 11.3 | — |
| 0° C. | 12.0 | — | 11.8 | — |
| −20° C. | 11.9 | — | 12.7 | — |
| Heat Deflection Temperature at 264 psi (°C.) | 69° | — | 79° | 60° |
| Coefficient of Thermal Expansion (in/in °F.)[2] | $5.2 \times 10^{-5}$ | — | $3.8 \times 10^{-5}$ | — |
| Linear Mold Shrinkage [2] (%) | 1.6 | | 1.0 | |
| 1.5 - | | | | |
| Percentage Residual Monomer | 0.1 | 0.03 | 0.08 | 3.0 |

[1] Value in the direction parallel to the direction of flow.
[2] Value is the average of the values obtained perpendicular to the direction of flow and parallel to the direction of flow.

EXAMPLE 34

A catalyst component is prepared in the following manner:

In an argon filled glove box, 3.96 g. of $WCl_6$ is weighed into a 10 oz. bottle. The bottle is then capped. In another 10 oz. bottle, 2.21 g. (10 mmol) of nonylphenol is added. This bottle is then capped and sparged with nitrogen for 20 minutes. The nonylphenol is then dissolved in 100 ml. of toluene, and the resulting solution is transferred by cannula to the bottle containing $WCl_6$. After marking the solvent level, the bottle is stirred and sprayed with nitrogen for one hour. Acetylacetone, 2.0 gram (20 mmol) is then added by syringe and the mixture is sparged rapidly and stirred overnight. Toluene is then added to restore the solvent level and the resulting solution is divided among ten 4" polyethylene tubes that are capped and sparged. These are stored under nitrogen.

An activator component is prepared in the following manner:

A 4" glass polymerization tube is capped and sparged. 8 ml. of toluene is syringed into the tube. 2.0 ml. of a 1.8M solution of diethyl aluminum chloride in toluene is added by a syringe. 0.49 grams of butyl ether is then added by syringe.

The polymerization is accomplished in the following manner:

A 15×125 mm test tube is capped with a rubber stopper and sparged with $N_2$. The tube is then charged with 5 ml. of DCPD. 0.19 ml. of the catalyst component and 0.038 grams of butyl ether are added by syringe. Then, 0.15 ml. of the activator component was added by syringe and the sample is shaken several times to mix the components. The mixture is allowed to stand and polymerize.

The percent gel swell is determined by the following method:

A 5 gram sample of the polymer was broken out of its test tube and sliced into approximately 1 cm.×1.3 cm. diameter cylinders. Each slice was then weighed and placed on a stainless steel wire. The wire and sample are hung in about 50 ml. of toluene in a 1 liter round bottom flask and the toluene is allowed to reflux overnight. After cooling, the samples are removed from the flask, patted dry, and weighed. Percent gel swell is determined according to the following equation:

$$\text{Percent Gel Swell} = \frac{\text{Final polymer weight} - \text{initial polymer weight}}{\text{initial polymer weight}} (100)$$

It is found that the sample has a percent swell of 110%.

EXAMPLE 34A

The procedure of Example 34 is followed except that a noncycloolefin solvent free mixture of $WCl_6$ and $WCl_4O$ in a 1:1 ratio stabilized by 2,4-pentanedione is used as the catalyst in place of $WCl_6$ and polymerzation is by injection of a mixture of half of the DCPD and the catalyst as a mixture and simultaneous injection of a mixture of half of the DCPD and the activator component as a mixture. Both DCPD mixtures are injected into a mold to form a flat plate of substantially crossliked solid thermoset polymer product. The procedure of Example 34A is repeated with the addition of 20% milled glass.

Polymer Properties

The product polymers of the invention as produced in Example 34A has an unusual balance of high modulus along with low residual monomer and good impact properties (Table 11). Preferably, the product polymers have less than one percent and more preferably less than 0.5 percent solvent other than residual monomer. Residual monomer is preferably less than two percent. The flexural modulus for unfilled polymer is 1,790 to 2,070 MPa, which is above typical properties for other RIM materials. MPa representing 1000 pounds per square inch absolute pressure. Addition of 20% milled glass raises the modulus to about 2,760 MPa in the mold flow direction and 2,480 MPa in the perpendicular direction. The somewhat different properties are due to glass fiber alignment. Higher levels of glass are possible, with the maximum determined by equipment limitations. Other fillers such as flaked glass, wollastonite, and calcium carbonate have also been successfully employed.

The falling-weight impact for unfilled material is 13 to 16 joules. This decreases to only 11 to 13 joules at −29° C. Impact failure is by ductile break at room temperature and approaches the brittle/ductile transition region at −29° C. The impact for 20% milled glass-filled material is 11 to 13 joules at both ambient temperatures and −29° C. In this case, the low-temperature failure is by brittle fracture.

Poly(dicyclopentadiene) has a glass transition temperature of 90° C. Heat sag values, which are important for automotive applications, average about 15 mm parallel to the flow direction and 23 mm perependicular to flow in a 20% glass-filled system. Coefficients of linear expansion are similar to those of other plastics.

In addition to beneficial physical properties, poly(dicyclopentadiene) exhibits excellent paintability characteristics. This is somewhat surprising considering the hydrophobic nature of the polymer. Formulations to provide flame-retardant properties have also been developed.

such as esters of carboxylic acids and also norbornene derivatives which are nonpolar hydrocarbons.

This results in copolymers which have a higher maximum use temperature than the homopolymer. These copolymers are more suited for applications where the plastic part made from the polymer must retain its properties at temperatures near 100° C., for applications where the part must be painted and the paint must be baked after application in an oven for a short period of time, or for applications where the plastic part must be heated in an oven for a short period of time to post-cure the polymer.

The glass transition temperature (Tg) of a polymer is defined as the temperature at which the modulus of the polymer decreases very rapidly as the polymer undergoes a transition from the glassy state to the rubbery state. In general, the glass transition temperature of a polymer will be raised by either increasing the crosslink density of the polymer or by increasing the stiffness of the chains in the backbone of the polymer. The crosslink density of a polymer may be determined by swelling the sample in a suitable solvent and then drying it. The average molecular weight between crosslinks can be calculated from the amount the polymer swells. The molecular weight between crosslinks can also be calculated by dynamic mechanical analysis from the storage modulus (G') above the sample's Tg. The relative crosslink density of two similar polymer samples can also be determined with swelling experiments. The more highly crosslinked a polymer is, the less it will swell relative to another sample of a similar polymer in the same solvent.

TABLE 11

Poly(dicyclopentadiene) Properties

| | Direction to Flow | Unfilled | 20% Milled Glass[a] |
|---|---|---|---|
| Flexural modulus, MPa | Parallel | 2,070 | 2,900 |
| | Perpendicular | | 2,480 |
| Flexural strength, MPa | Parallel | 62 | 62–76 |
| | Perpendicular | | 62 |
| Tensile modulus, MPa | | 1,620 | |
| Tensile strength, MPa | Parallel | 34 | 31 |
| Tensile elongation, % | Parallel | 80 | 25 |
| Glass transition temperature, °C. | | 90 | |
| Heat sag, 152 mm OH, | Parallel | 61 | 10–20 |
| 1 hr., 135° C., mm | Perpendicular | | 15–30 |
| Coefficient of linear | Parallel | $37 \times 10^{-6}$ | $17 \times 10^{-6[b]}$ |
| expansion, mm/mm/° C. | Perpendicular | | $34 \times 10^{-6[b]}$ |
| Mold shrinkage, cm/cm | Parallel | 0.035 | 0.008 |
| | Perpendicular | | 0.021 |
| Falling weight impact, | | | |
| joules, 23° C. | | 13–16 | 11–13 |
| −29° C. | | 11–13 | 11–13 |
| Flash point of percent residual monomer | | 0.2 | 0.04 |
| Catalyst mixture with DCPD | | 101 | 101 |
| Activator mixture with DCPD | | 100 | 100 |

[a] 1/16 in. OCF 737.
[b] Retained on recycle.

Copolymers

By the addition of comonomers, the glass transition temperature (Tg) of polydicyclopentadiene made by ring-opening polymerization is raised. Included in the comonomers which are effective are comonomers which increase the crosslink density of the polymer, or increase the "stiffness" of the backbone chain of the polymer. Effective comonomers include substituted norbornenes which contain polar functional groups Poly(dicyclopentadiene) formed by ring-opening polymerization in RIM has been found by swelling experiments, and by dynamic mechanical experiments, to have approximately one crosslink for every three repeat units in the polymer chain. In order to raise the Tg of the polymer, a comonomer may be added that will either have two or more strained, reactive double bonds that will open during the polymerization, so that the number of crosslinks will be increased, or it will contain four or more rings so that when it becomes incorporated in the polymer chain, rotation or movement of the resulting backbone will be more constrained, or in other words the chain will be stiffer.

Dicyclopentadiene may be copolymerized with about 0 to 50% by weight of another cycloolefin. More preferably the other cycloolefin is from about 1 to 30% by weight. Most preferably the other cycloolefin is from about 1 to 25% by weight and the cycloolefin is one or more norbornene-type monomers. Some of the copolymers particularly those having other norbornene-type monomers have a glass transition temperature (Tg) which is higher than the Tg for polymerized dicyclopentadiene. Useful norbornene-type monomers include the 1:1 Diels-Alder adducts of cyclopentadiene with norbornene, norbornadiene and 1,5-cyclooctadiene, the adducts of cyclopentadiene with polyfunctional acrylates, such as trimethylolpropane triacrylate, ethylene glycol diacrylate, ethylene glycol dimethacrylate, 1,4-butane-diol dimethacrylate and 1,4-butanediol diacrylate, and the 2:1 adduct of cyclopentadiene with diallyl adipate. Other monomers which have two or more strained, reactive double bonds in the same molecule would also be suitable. Substantial increases in the crosslink density (as measured by the degree of swelling of the copolymers) are obtained with copolymers made from DCPD and the cyclopentadiene adducts with norbornadiene, trimethylolpropane triacrylate, ethylene glycol diacrylate and ethylene glycol dimethacrylate. Excellent results are obtained with the adduct of cyclopentadiene and norbornadiene.

Preparation of Comonomers
1,4,5,8-Dimethano-1,4,4a,5,8,8a-hexahydronaphthalene (DMHN)

DMHN is prepared by reacting bicyclo [2.2.1]-2,5-heptadiene (norbornadiene) with cyclopentadiene according to reaction I as follows:

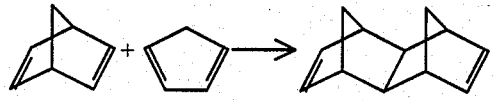

EXAMPLE 35

Norbornadiene (5.0 kg) was charged to a five gallon autoclave while maintaining an inert nitrogen atmosphere in the autoclave. DCPD (1.35 kg) was then charged to the reactor.

The reactor was then heated to 180° C. over five hours while stirring, and then maintained at 180° C. for sixteen hours. The reactor was then cooled to room temperature, after which the reactor was vented and opened and the contents of the reactor removed. The DMHN was purified by distillation in a packed column. Excess norbornadiene ($BP_{70}=38°$ C.) is removed first by distilling at a pressure of 70 torr. DMHN ($BP_{10}=90°$ C.) is then purified by distilling at 10 torr to obtain 1.84 kg of product.

Tricyclo [8.2.1.0]trideca-5,11-diene (TTD)

TTD is prepared by reacting 1,5-cyclooctadiene with cyclopentadiene according to reaction II as follows:

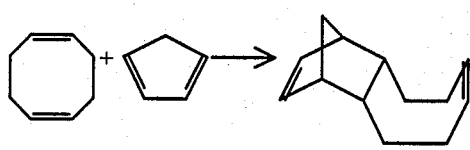

EXAMPLE 36

Dicyclopentadiene (50 grams) and 150 grams of 1,5-cyclooctadiene were added by cannula to a sparged pop bottle. The mixture was then heated to 190° C. over 2 hours and then maintained at that temperature for 4 hours and then allowed to cool. TTD was purified by first distilling our excess 1,5-cyclooctadiene at a pressure of 5 torr and then distilling the TTD ($BP_{05}=80°$ C.) at 0.03 torr to give 63 grams of product.

Trimethylolpropane-tris-(5-norbornene-2-carboxylate) (TPNC)

TPNC is prepared by reacting trimethylolpropane triacrylate with cyclopentadiene according to reaction III as follows:

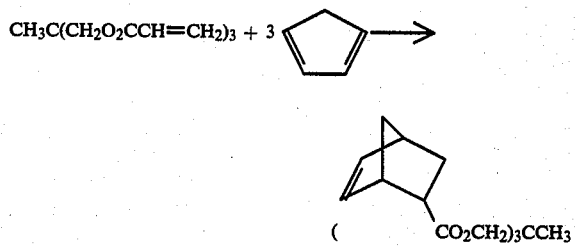

EXAMPLE 37

A solution of 14.8 grams of trimethylolpropane triacrylate in 150 ml of methylene chloride was sparged with nitrogen for 15 minutes. Cyclopentadiene (42.8 ml, 0.52 moles) was added in one portion by syringe, after which the mixture was heated to 40° C. for 3 hours. After cooling, the methylene chloride and excess cyclopentadiene were removed by rotary evaporator and high vacuum to provide the product.

Ethylene-bis-(5-norbornene-2-carboxylate) (ENC)

ENC is prepared by reacting ethylene glycol diacrylate with cyclopentadiene according to reaction IV as follows:

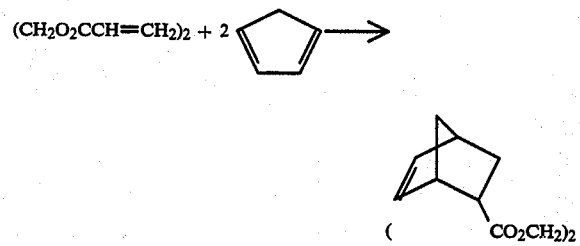

EXAMPLE 38

A solution of 17.0 g (0.100 moles) of distilled ethylene glycol diacrylate in 200 ml of methylene chloride was sparged with nitrogen in a 0.5 l reactor. Cyclopentadiene (46 g, 0.70 moles) was added in one portion by syringe, after which the mixture was heated to 40° C. for 4 hours under a nitrogen atmosphere. The mixture was then cooled, after which the methylene chloride and excess cyclopentadiene were removed with a rotary evaporator. The crude product was purified by chromatography on a column of 100 g of neutral alumina, eluting first with 1.5 l of hexane and then with 4 l of a 1:1 mixture of hexane and methylene chloride. The hexane/methylene chloride was then stripped to provide the pure ENC.

Ethylene-bis-(2-methyl-5-norbornene-2-carboxylate (EMNC)

EXAMPLE 39

EMNC is prepared by first adding a solution of 21.0 g (0.200 moles) of methacryloyl chloride in 50 ml of ether to a solution of 26 g (0.39 moles) of cyclopentadiene in 50 ml of ether over one hour at 0° C. The mixture was then warmed to room temperature and stirred overnight. This solution was then transferred by cannula to a 0° C. solution of 6.10 g (0.983 moles) of ethylene glycol and 25 g (0.32 moles) of pyridine in 150 ml of methylene chloride. This mixture was then stirred overnight while warming to room temperature. The solution was then decanted away from precipitated salts which were washed with two 50 ml portions of hexane. The organic layer was washed with 200 ml of 5% KOH in saturated aqueous NaCl, dried over magnesium sulfate and concentrated on a rotary evaporator. The crude product was purified by chromatography on alumina by eluting first with 200 ml of hexane followed by one liter of methylene chloride. Evaporation of the methylene chloride provided 12.5 grams of EMNC.

1,4-Butane-bis-(2-methyl-5-norbornene-2-carboxylate) (BMNC)

EXAMPLE 40

BMNC is prepared by first adding a solution of 15.5 g (0.148 moles) of methacryloyl chloride in 25 ml of ether to a solution of 15 g (0.23 moles) of cyclopentadiene in 25 ml of ether over one hour at 0° C. The mixture is then warmed to room temperature and stirred overnight. This solution is then transferred by cannula to a 0° C. solution of 6.66 g (0.107 moles) of ethylene glycol and 20 g (0.253 moles) of pyridine in 180 ml of methylene chloride. This mixture is then stirred overnight while warming to room temperature. The solution is then decanted away from precipitated salts which are washed with two 50 ml portions of hexane. The organic layer is washed with 200 ml of 5% KOH in saturated aqueous NaCl, dried over magnesium sulfate and concentrated on a rotary evaporator. The crude product is purified by chromatography on alumina by eluting first with 100 ml of hexane followed by 600 ml of methylene chloride. Evaporation of the methylene chloride provided 12.5 grams of BMNC.

Bis-(20Hydroxymethyl-5-norbornene Adipate (HMNA)

EXAMPLE 41

A solution of 227.5 grams of adipoyl chloride in 1 liter of ether was cooled to 0° C. in a 3 liter reactor. A solution of 31.7 grams of 5-hydroxy-methyl-2-norbornene in 227.5 ml of pyridine was added slowly over a period of two hours. The mixture was stirred overnight and filtered. The solids were then washed with hexane which was combined with the filtrate and washed with 1 liter of dilute HCl solution, 250 ml of saturated NaCl solution and dried over magnesium sulfate. After removal of solvent and other volatiles, the crude product is purified by chromatography on alumina to give 271 grams of HMNA.

The adduct of cyclopentadiene and norbornene contains only one double bond and thus will not increase the crosslink density of the resulting copolymer. However, the comonomer is a tetracyclic monomer so that in the ring-opened copolymer the repeat unit in the polymer chain will contain three fused rings. These tricyclic units have considerably less free rotation, and therefore less flexibility, than DCPD so that their presence results in a stiffer polymer chain and a correspondingly higher Tg. Similar results should be obtained with the cyclopentadiene adducts of alkylnorbornenes such as 5-methylnorbornene.

1,4,5,8-Dimethano-1,4,4a,5,8,8a-octahydronaphthalene (DMON)

DMON is prepared by reacting norbornene with cyclopentadiene according to reaction V as follows:

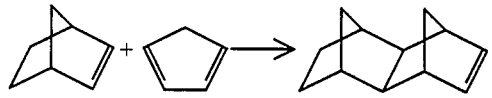

EXAMPLE 42

Norbornene (76 g, 0.807 moles) is weighed into a 10 oz bottle which is then capped and sparged. DCPD (54 ml, 0.439 moles) was added by syringe. The mixture was heated to 180° C. for 16 hours, after which the bottle was cooled to room temperature and opened. Excess norbornene was removed by distillation after which the product was distilled under nitrogen in a pop bottle to give 41.7 g of DMON.

Preparation of Copolymers Copolymers of DCPD

EXAMPLE 43

A 0.1M solution of a tungsten catalyst is prepared by weighing 3.96 grams of WCl$_6$ under nitrogen into a 200 ml bottle. Nonyl phenol (2.21 grams, 0.01 moles) dissolved in 100 ml of toluene, that had been distilled from Na/K alloy under nitrogen, is added, and the mixture is stirred for one hour while sparging with nitrogen. Acetylacetone (2.00 grams, 0.02 moles) is then added by syringe and the mixture was stirred overnight while sparging with nitrogen to remove HCl gas.

An aluminum alkyl activator solution is prepared by diluting 2.00 ml (0.00376 moles) of a 1.88M solution of diethylaluminum chloride (DEAC) with 8.00 ml of distilled toluene and 0.64 ml (0.0038 moles) of di-butyl ether.

Solutions are prepared containing measured mixtures of DCPD and DMHN. Into a 15 mm×125 mm test tube that had been capped with a rubber septum and sparged with nitrogen is syringed 5 grams of one of the solutions of the comonomers. The aluminum alkyl activator (0.15 ml, 0.054 mmoles) is added to the monomers by syringe. Next, 0.15 ml of di-butyl ether was added. After a thermocouple probe has been inserted to measure the exotherm of the reaction, 0.19 ml (0.019 mmoles) of 0.1M tungsten catalyst is added and the tube is quickly shaken to mix the reactants. After a short period of time the mixture polymerized into a solid infusible polymer mass. Table 12 gives values for the % insoluble gel, % swell in toluene, and Tg, as determined by differential scanning calorimetry, of the copolymers.

TABLE 12

| wt. % DMHN | % Gel | % Swell | Tg |
|---|---|---|---|
| 0 | 97 | 110 | 140 |
| 5 | 94 | 67 | 175 |
| 10 | 93 | 52 | 187 |
| 20 | 93 | 40 | 196 |

EXAMPLES 44 and 45

These examples describe the preparation of a copolymer of 10 wt % DMHN and 90 wt % DCPD by reaction injection molding (RIM). Samples of DCPD copolymers made by RIM processing were made using a standard RIM machine supplied by Accuratio Co. of Jeffersonville, Ind. The following description illustrates the standard procedure for molding samples. First the two monomer storage tanks on the machine were closed off and inerted with nitrogen. The tanks are located on different sides of the RIM machine: the tank on the A side is the one to which the activator was later added and the tank on the B side is the one to which the catalyst was later added.

A mixture of 90% DCPD and 10% DMHN, containing 6% by weight of Stereon 720 styrene-butadiene rubber, was added to both tanks. If desired, solid fillers such as milled glass fiber or Wollastonite can be added. Sufficient diethylaluminum chloride was transferred into the A tank so that the concentration was 0.048M and sufficient di-n-butyl ether was added so that the ether to aluminum ratio was 1.5:1. Next, sufficient tungsten catalyst solution was added to the B side tank to bring the concentration of catalyst to 0.0071M. All transfers were done and all materials were handled in a way to preclude the entrance of oxygen or moisture into the system. The materials were then thoroughly blended in their respective tanks.

The mixing of the A stream and the B stream was accomplished using a standard impingement type RIM mixhead. The ratio of the activator/monomer solution mixed with the catalyst/monomer solution was 1:1. The impingement mixing was accomplished by passing both the solutions through orifices 0.032" in diameter at a flow rate approximately 80 ml/sec. This required pumping pressures of approximately 1000 psi.

The resulting mixture flows directly into a mold heated to between 50° and 60° C. The mold has a flat cavity that forms a plaque sample 10"×10"×⅛" thick. The mold was opened and the finished plaque was removed approximately 10 to 30 seconds after the mold was filled. In Example 10, the procedure outlined above was followed to give plaques that could be removed from the mold in 15 seconds. In Example 11, 1/16" milled glass fiber was added to the monomer solutions so that the samples contained 20% glass. These samples were made by initially slurrying the glass into both the catalyst/monomer and the activator/monomer solutions. The physical properties for these samples are shown in Table 13.

TABLE 13

| | Example 10 | Example 11 |
|---|---|---|
| % Glass Filler | 0 | 20 |
| Flex Modulus (kpsi) | | |

TABLE 13-continued

| | Example 10 | Example 11 |
|---|---|---|
| 23° C. | 224 | 421 |
| 100° C. | 66 | 187 |
| Flex Strength (kpsi) | | |
| 23° C. | 9.6 | 10.7 |
| 100° C. | 1.4 | 2.0 |
| Plate Impact Energy (ft-lb) | | |
| 23° C. | 8.4 | 9.1 |
| −29° C. | 3.8 | 9.0 |

Copolymers of DCPD and TTD

EXAMPLE 46

The procedure of Example 9 is followed except that TTD is used as the comonomer with DCPD. A solid infusible polymer mass was obtained. The % insoluble gel, % swell in toluene and Tg, as determined by dynamic mechanical analysis, for these copolymer samples are shown in Table 14.

TABLE 14

| wt. % DMHN | % Gel | % Swell | Tg |
|---|---|---|---|
| 5 | 99 | 108 | |
| 10 | 99 | 103 | |
| 20 | 98 | 94 | 145 |

Copolymers of DCPD with Ester-Containing Monomers

EXAMPLES 47–51

An aluminum alkyl activator solution is prepared by diluting 2.00 ml (0.00376 moles) of a 1.88M solution of diethylaluminum chloride (DEAC) with 8.00 ml of distilled toluene. The procedure of Example 9 is followed except that the above aluminum alkyl activator solution is used and no di-n-butyl ether is added to the monomers. In addition, the solution of monomers is heated to 60° C. immediately upon addition of the tungsten catalyst solution by placing the tube in a 60° C. heating bath. The comonomer, % comonomer, % insoluble gel, % swell in toluene and Tg, as determined by dynamic mechanical analysis, for the copolymers are given in Table 15.

TABLE 15

| Example | Comonomer | % Comonomer | % Gel | % Swell | Tg |
|---|---|---|---|---|---|
| 47 | TPNC | 5 | 95 | 93 | 158 |
| | | 10 | 94 | 63 | |
| | | 20 | 94 | 58 | 165 |
| 48 | ENC | 5 | 95 | 95 | |
| | | 10 | 94 | 85 | |
| | | 20 | 92 | 71 | 153 |
| 49 | EMNC | 5 | 93 | 107 | |
| | | 10 | 94 | 89 | |
| | | 20 | 94 | 79 | |
| 50 | BMNC | 5 | 97 | 94 | |
| | | 10 | 97 | 90 | |
| | | 20 | 95 | 81 | 138 |
| 51 | HMNA | 5 | 98 | 100 | |
| | | 10 | 98 | 87 | |
| | | 20 | 94 | 76 | 122 |

Copolymers of DCPD with DMON

EXAMPLE 52

The procedure of Example 43 is followed except that DMON is used as the comonomer with DCPD in place of DMHN. A solid infusible polymer mass is obtained in all cases. Table 16 gives the % insoluble gel, % swell in toluene, and Tg, as determined by differential scanning calorimetry for these copolymer samples.

TABLE 16

| Comonomer | % Gel | % Swell | Tg |
|---|---|---|---|
| 5 | 97 | 110 | |
| 10 | 100 | 105 | 160 |
| 20 | 98 | 120 | 167 |
| 100 | 94 | 102 | 195 |

Other features, advantages and specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

EXAMPLES 53-59

In Examples 53-59, substantially crosslinked dicyclopentadiene polymer and copolymer products are formed. The products are formed by mixing a catalyst solution and an activator solution to form a polymerization solution which polymerizes to form the polymer products as described in Table 17. The catalyst solution on a molar basis is tungsten catalyst in monomer. The tungsten catalyst is made as follows: t-butanol is stirred with 20 grams of $WCl_6$ in 70 ml of dry toluene under $N_2$ atmosphere in a t-butanol to $WCl_6$ molar ratio of 0.50 to form a 0.841M catalyst solution of $WCl_6$ and $WOCl_4$. The molar ratio of $WCl_6$ to $WOCl_4$ formed is about 3 to 1. 11.1 grams of nonyl phenol in 30 ml of toluene is then added. 10.1 grams of 2,4-pentanedione is then added by syringe. This solution is then sparged 18 hours with $N_2$ to remove HCl. 10 ml of monomer is then added to 0.30 ml of the catalyst solution. The monomer and catalyst solution is then warmed at 35° C. for 24 hours while sparging with nitrogen to evaporate the toluene and phenol to form a substantially solvent free monomer solution of catalyst. The activator solution is prepared by combining under $N_2$ 8.6 ml of monomer and 0.39 ml of 1.0M tri-n-octyl-aluminum in monomer.

In Examples 53-59, the activator solution also includes 0.1 ml of bis-(2-methoxyethyl) ether. The exotherm of polymerization occurs in about 15 to 25 seconds after mixing 5.0 ml the catalyst in monomer solution to 5.0 ml of the activator in monomer solution. Both solutions are initially at 25° C. They are intimately mixed in the mixed in the mixed and the mixture injected into a mold.

In Examples 53 and 56 flame retardant is added to the catalyst solution prior to mixing with the activator solution. In Examples 55, 58 and 59 milled glass is added to the activator solution prior to mixing with the catalyst solution. In Examples 56-59 elastomer is added equally to both the catalyst solution and the activator solution priro to mixing.

TABLE 17

| | Example | | | | | | |
|---|---|---|---|---|---|---|---|
| | 53 | 54 | 55 | 56 | 57 | 58 | 59 |
| Activator to Catalyst ratio | 3.0 | 3.0 | 3.0 | 3.0 | 3.0 | 3.0 | 3.0 |
| Monomer weight % | | | | | | | |
| DCPD | 100 | 80 | 80 | 95 | 95 | 95 | 95 |
| DMHN | — | 20 | 20 | 5 | 5 | 5 | 5 |
| Additive parts flame retardant N,N'—ethylene-bis-tetrabromophthalimide/$Sb_2O_3$/$NH_4BH_4$) per 100 parts monomer (by weight) | 32 | — | — | 32 | — | — | — |
| Weight % residual monomer | 0.1 | 0.3 | 0.04 | 0.4 | 0.4 | 0.05 | 0.05 |
| Tg °C. | 140 | 196 | 198 | 175 | 175 | 175 | 175 |
| Weight % swell | 100 | 40 | 38 | 60 | 60 | 60 | 60 |
| Weight % gell | 98 | 93 | 99.9 | 89.5 | 89.5 | 89.9 | 89.9 |
| Flexural modulus (psi) | 380,000 | 300,000 | 576,000 | 385,000 | 245,000 | 526,000 | 546,000 |
| Notched Izod impact strength (ft-lb/inch notch) | 2.1 | 2.0 | 2.3 | 10.5 | 8.8 | 10.2 | 8.9 |
| Filler weight % ⅛ inch milled glass | — | — | 33 | — | — | 33 | 33 |
| Elastomer styrene-butadiene | | | | | | | |
| weight % butyl rubber | — | — | — | 6 | — | 6 | — |
| weight % | — | — | — | — | 10 | — | 10 |
| weight % saturated styrene | | | | | | | |
| weight % butadiene-styrene | | | | | | | |
| weight % triblock rubber | | | | | | | |

Rate Moderation By Use of Polar Monomer

EXAMPLE 60

Synthesis of 2-Hydroxymethyl-5-Norbornene Acetate

Into a solution of 99.2 g of 2-hydroxymethyl-5-norbornene and 50 ml of chloroform is added dropwise a solution of 84.0 g of acetic anhydride in 100 ml of chloroform. This mixture is allowed to stir overnight at room temperature, followed by heating at reflux for three hours. The cooled reaction mixture is poured into water and stirred to hydrolyze unreacted acetic anhydride. The layers are separated, the organic phase is diluted with an equal volume of hexane, and the mixture repeatedly washed with water to remove most of the pyridine. A final wash with dilute HCl solution, saturated sodium bicarbonate solution and saturated sodium chloride solution removes pyridine, acetic acid and water from the organic phase. Drying over anhydrous magnesium sulfate and removal of the solvent on a rotary evaporator affords 137 g of crude product as a faintly yellow, pleasant smelling oil. This is diluted with 2 volumes of hexane and passed through a 300 g column of neutral alumina, followed by continued hexane elution (1 l) until "no more" material was found in the effluent. Distillation of the hexane and vacuum distillation of the residue (55° C., 0.8 mm) provides 103.1 g (84%) of the acetate as a clear, colorless oil characteristic fruity odor; ir: 3139, 3061, 2965, 2868, 1741, 1361, 1235, 1028, 714 cm$^{-1}$; 60 MHZ NMR (CDCl$_3$) 2.02 ($H_3CCO_2-$).

EXAMPLE 61

Synthesis of 2-Hydroxymethyl-5-Norbornene Adipate

Into a solution consisting of 62.0 of the 5-hydroxymethyl-2-norbornene and 100 ml of pyridine under $N_2$ cooled to 0° C. is added dropwise a solution of 45.7 g (36.4 ml) of distilled adipoyl chloride (107° C./2 mm) in 200 ml of chloroform. The ice bath is removed after addition was completed, and the mixture stirred overnight at room temperature. The reaction mixture is diluted with 2 volumes of hexane and repeatedly washed with dilute aq. HCl solution to remove the pyridine. This is followed by saturated sodium bicarbonate washes, saturated NaCl solution, and drying over anhydrous magnesium sulfate. Removal of the solvent gives 95.53 g (104%) of crude product as a pleasant smelling yellow oil. The crude product is distilled under vacuum (206°/0.4 mm) to give 93.82 g (82%) of product as a nearly colorless and odorless oil. Dilution of this material with 2 volumes of hexane and elution through 250 g of neutral alumina, continued elution with hexane and solvent stripping at reduced pressure finally gave a water white product in 75% yield; ir: 3120, 3061, 2965, 2870, 1735, 1170, 714 cm$^{-1}$.

EXAMPLE 62

Synthesis of Methyl 5-Norbornene-2-Carboxylate

In 100 ml of anhydrous ether at 0° C. is mixed 30 ml of cyclopentadiene and 32 ml of methyl acrylate. The ice bath is removed and the mixture allowed to stir overnight. The solvent, unreacted methyl acrylate, and cyclopentadiene are removed at ambient temperature at reduced pressure; as less material distilled out of the mixture the pressure is gradually reduced to 0.5 mm. The desired epimeric mixture of methyl carboxylate is distilled at 42'-43° and 0.5 mm; ir: 3118, 3060, 2965, 2941, 2862, 1734, 1428, 1329, 1264, 1190, 1024, 704, cm$^{-1}$; 60 MHZ NMR: endo/exo=80/20.

The rate of cycloolefin polymerization can be adjusted by use of polar monomers such as norbornene esters. Copolymers of DCPD and norbornene esters are polymerized in from about one to two and one fourth minutes without the addition of a noncycloolefin rate moderate as shown in Examples 63–65 and Table 18. The copolymers have percent by weight gel of from about 88.7 to 99.2 as shown in Table 19.

EXAMPLES 63–65

Catalyst Preparation

In an Argon-filled glove box, 3.96 g of WCl$_6$ is weighed into one 10 oz pop bottle and 19.80 g into another for preparation of 0.1M and 0.5M solutions, respectively. These bottles are then removed from the box and placed in a $N_2$ filled glove bag. Into one centrifuge bottle is weighed 2.00 g of nonylphenol (C$_9$PhOH) and 10.00 g into another. The bottles are then filled with 100.0 ml of toluene (from Na/K), capped and sparged with $N_2$ for 30 minutes. The contents of the bottles are transferred via cannula under positive $N_2$ pressure into their respective WCl$_6$ bottles to form the 1:1 complexes followed by $N_2$ sparing overnight to remove evolved HCl. The contents of the 0.1M WCl$_6$/C$_9$ PhOH bottle are distributed in 9 4" poly tubes (previously $N_2$ sparged) in a glove bag. The DEAC (Et$_2$AlCl) solution is used as received (25% wt in toluene), or a known volume is transferred to a 4" poly tube (previously capped and sparged) and the calculated amount of n-Butyl ether added to form the 1:1.1 Al/Bu$_2$O complex.

Copolymerization of DCPD and Functional Monomers

A typical procedure for copolymerization of DCPD and an ester comonomer is as follows: Six 1×13 cm test tubes are loaded with the indicated weight % of functional comonomer, a rubber septum was wired on, and the assembly sparged with $N_2$ for 10 minutes. Enough dicyclopentadiene is then added to bring the contents of the tubes to 5.0 g and sparging continued for 10 minutes. To each tube immediately prior to polymerization is added 0.03 ml of 1.84M DEAC in toluene, and the contents thoroughly mixed. A solution of 0.5M WCl$_6$/C$_9$PhOH in toluene (0.04 ml) is then added, the contents are mixed by multiple inversions (15 sec), a thermocouple probe (soldered into a 14 ga syringe needle) inserted through the top, and the tube placed in a 60° C. oil bath to initiate polymerization. The times reported in the table are for reaching the exotherm maximum from time of immersion in the oil bath; precision is within the ±10 sec envelope. A sample without catalyst will take 2 minutes to reach bath temperature from time of immersion.

Gel Swell Determinations on Comonomers

The general procedure used is as follows: A 5 g sample of copolymer is removed from its test tube (by breaking the glass) and carefully sliced into 1–2 mm thick sections across the cylindrical axis with a band saw. The burrs are removed, each slice weighed to the nearest milligram, and strung onto a stainless steel wire taking care to keep them in known sequence. This is done for each sample at a given comonomer feed. The wire is made into a closed loop and placed in 50 ml of toluene for each gram of copolymer. Whereas, in some cases, several loops of copolymer are placed in a single flask of toluene, only those of common functional monomer are ever placed together. These flasks are then heated to reflux for 16 hours (overnight) and cooled. Each loop is successively removed from the flask and placed in a small crystallizing dish of fresh toluene. The slices are removed, patted dry, and weighed individually, again taking care not to not to disturb their sequence or to tear the swollen samples. After weighing, they are restrung and placed in a forced draft ($N_2$) oven at 135° C. for 16 hours (overnight). The samples are reweighed and their gel and swell values calculated.

Two samples are reacted under each set of comonomer composition. Each sample is then sliced into thin sections for gel/swell determinations.

TABLE 18

Copolymerization of Dicyclopentadiene and Functional Monomers[a]

| Example | Comonomer (CM) | DCPD/CM (wt %) | $T_{max}$ (°C.) | Time tp $T_{max}$ (min) |
|---|---|---|---|---|
| 63 |  CH₂OCOCH₃ | 95/5 | 201 | 1¾ |
| | | 95/5 | 190 | 1¼ |
| | | 90/10 | 206 | 1½ |
| | | 90/10 | 202 | 1½ |
| | | 80/20 | 198 | 1½ |
| | | 80/20 | 198 | 1½ |
| 64 |  CH₂OCOCH₂CH₂)₇ | 95/5 | 203 | 1 |
| | | 95/5 | 204 | 1 |
| | | 90/10 | 205 | 1½ |
| | | 90/10 | 206 | 1½ |
| | | 80/20 | 197 | 2¼ |
| | | 80/20 | 205 | 2 |
| 65 |  CO₂CH₃ | 95/5 | 199 | 1 |
| | | 95/5 | 199 | 1 |
| | | 90/10 | 204 | 1 |
| | | 90/10 | 201 | 1 |
| | | 80/20 | 203 | 1¼ |
| | | 80/20 | 206 | 1¼ |
| | Homopolymerization of DCPD (Room Temperature Initiation) | 100/0 | 194 | ¾ |

[a] All polymerizations are run with the same concentration of catalysts, calculated as 2000:1:2.75 Monomer:W:Al based on 5 g of DCPD. All reactions are run in a 60° C. oil bath except homopolymerization of DCPD (last entry). Times recorded are from immersion of sample tube in the bath to the maximum temperature of the exotherm. A tube with no catalyst requires 2 minutes to reach bath temperature.

TABLE 19

Gel-Swell Values for Copolymers of DCPD and Functional Monomers

| Example | Comonomer (CM) | DCPD/CM (wt %) | Swell (Weight %) | Gel (Weight %) |
|---|---|---|---|---|
| 63 |  CH₂OCOCH₃ | 95/5 | 153 | 95.3 |
| | | 95/5 | 152 | 92.8 |
| | | 90/10 | 184 | 95.0 |
| | | 90/10 | 144 | 93.8 |
| | | 80/20 | 213 | 89.1 |
| | | 80/20 | 190 | 88.7 |
| 64 |  CH₂OCOCH₂CH₂)₇ | 95/5 | 95 | 98.2 |
| | | 95/5 | 105 | 98.6 |
| | | 90/10 | 86 | 97.9 |
| | | 90/10 | 88 | 97.6 |
| | | 80/20 | 77 | 94.8 |
| | | 80/20 | 75 | 93.8 |
| 65 |  CO₂CH₃ | 95/5 | 122 | 96.0 |
| | | 95/5 | 113 | 94.7 |
| | | 90/10 | 200 | 97.3 |
| | | 90/10 | 127 | 98.9 |
| | | 80/20 | 186 | 97.0 |
| | | 80/20 | 245 | 99.2 |

In Examples 66, 67, 71 and 73, the fluorinated alkyl methacrylate copolymer surfactant used is FC-740, manufactured by Minnesota Mining and Manufacturing Company.

EXAMPLE 66

The catalyst used is a 1:1 molar mixture of WCl₆ to WCl₄O as prepared herein above. An aluminum alkyl activator solution that is 1.06M in trioctylaluminum (TNOA), 0.19M in diethylaluminum iodide (DEAI) and 1.25M in methoxyethyl ether is prepared by dissolving 85.0 grams of methoxyethyl ether, 196.1 grams of TNOA, and 20.00 grams of diethylaluminum iodide (DEAI) in 157.3 ml of dicyclopentadiene. The molar ratio of TNOA to DEAI to methoxyethyl ether is then 0.85:0.15:1.00.

Examples 67 through 70 illustrate small scale examples where a cellular polymer of dicyclopentadiene monomer is formed using a mixture of diethylaluminum iodide and trioctylaluminum as catalyst activators where the dicyclopentadiene monomer also contains 6 weight percent styrene-butadiene rubber.

EXAMPLE 67

A catalyst and monomer solution is prepared by mixing under nitrogen 50 grams of DCPD that had previously had 3.0 grams of styrene-butadiene rubber dissolved in it with 3.8 ml of the 0.1M catalyst solution, 2.5 grams of trichlorofluoromethane, and 0.50 grams of fluorinated alkyl methacrylate copolymer.

An activator and monomer solution is prepared by mixing under nitrogen 50.0 grams of DCPD that has 3.0 grams of styrene-butadiene rubber dissolved in it with 1.45 ml of 1.25M aluminum alkyl activator solution, 2.5 grams of trichlorofluoromethane, and 0.50 grams of fluorinated alkyl methacrylate copolymer.

The catalyst and monomer and activator and monomer were then combined and mixed rapidly under nitrogen. The mixture was then poured rapidly into a vented mold and allowed to polymerize into a cellular polymer.

EXAMPLE 68

The procedure of Example 2 is followed except that ten percent of trichlorofluoromethane was used as the blowing agent, 0.5 percent fluorinated alkyl methacrylate copolymer surfactant was used and 1.16 ml of the aluminum alkyl activator is used to make up the activator and monomer solution.

EXAMPLE 69

The procedure of Example 2 was followed except that seven percent trichlorofluoromethane was used as the blowing agent and 1.40 ml of aluminum alkyl activator solution is used to make up the activator and monomer solution.

EXAMPLE 70

The procedure of Example 2 was followed except that 1.51 ml of aluminum alkyl activator solution is used to make up the activator and monomer solution.

EXAMPLE 71

The procedure of Example 3 is used except that fifteen percent methylene chloride was used as the blowing agent and 1.06 ml of aluminum alkyl activator solution is used to make up the activator and monomer solution.

Table 20 shows the polymerization mixtures from which foam products are formed in Examples 66–71.

TABLE 20

| | FOAM EXAMPLES | | | | |
|---|---|---|---|---|---|
| | Example 67 | Example 68 | Example 69 | Example 70 | Example 71 |
| DCPD (grams) | 100 | 100 | 100 | 100 | 100 |

TABLE 20-continued

FOAM EXAMPLES

| | Example 67 | Example 68 | Example 69 | Example 70 | Example 71 |
|---|---|---|---|---|---|
| Tungsten catalyst mmol | .756 | .756 | .756 | .756 | .756 |
| Diethylaluminum diodide (mmol) | .272 | .218 | .262 | .280 | .198 |
| Trioctyl aluminum (mmol) | 1.54 | 1.234 | 1.49 | 1.61 | 1.12 |
| Methoxyethyl ether (mmol) | 1.81 | 1.452 | 1.75 | 1.89 | 1.32 |
| Blowing Agent | CFC13 | CFC13 | CFC13 | CFC13 | CH2C12 |
| Weight percent | 5 | 10 | 7 | 5 | 15 |
| Rubber (elastomer) | SBR | SBR | SBR | SBR | SBR |
| Weight percent | 6 | 6 | 6 | 6 | 6 |
| Surfactant | FC-740 | FC-740 | FC-740 | FC-740 | FC-740 |
| Weight percent | 1.0 | 0.5 | 1.0 | 1.0 | 0.5 |
| Density (g/cc) | 0.30 | 0.13 | 0.21 | 0.39 | 0.18 |

EXAMPLE 72

This example illustrates a preferred embodiment of the synthesis of a cellular cross-linked polymerized dicyclopentadiene via reaction injection molding where the catalyst system is activated by a mixture of trioctylaluminum (TNOA) and diethylaluminum iodide (DEAI).

Into two tanks, which have previously been closed and inerted with nitrogen, having a capacity of two gallons each is charged DCPD containing 6% by weight of a random styrene-butadiene rubber. Sufficient $WCl_6$/nonylphenol/acetylacetone catalyst, having a ratio of 1:1:2, in xylene is added to one of the tanks to provide a DCPD:tungsten catalyst ratio of 1000:1. Next, to the other tank is added sufficient trioctylaluminum:diethylaluminum iodide:methoxyethyl ether solution, having a molar ratio of 0.85:0.15:1.0 to provide a DCPD:aluminum ratio of 1000:2.4. Fluorinated alkyl methacrylate copolymer surfactant is added to each tank to achieve a concentration of 0.5 parts per hundred, based on the weight of DCPD. Methylene chloride is then added to each tank to achieve a concentration of 5.0 parts per hundred, based on the weight of DCPD. All transfers are done in a way to preclude the entrance of oxygen or moisture into the system. The materials are then thoroughly blended in their respective tanks.

The components of the two tanks are combined in a standard impingement type RIM mixhead. The ratio of the activator/monomer solution mixed with the catalyst and monomer solution is 1:1. The impingement mixing is accomplished by passing both of the solutions through orifices 0.032 inch in diameter at a flow rate of approximately 80 ml/sec. This requires pumping pressure of approximately 500 psi to 1000 psi.

The resulting mixture flows directly into a mold heated to between 35° C. and 70° C. The mold is made out of chrome plated aluminum. The mold has a flat cavity which forms a plaque sample 8 inch×8 inch×⅜ inch thick. The reactants polymerize rapidly in the closed mold, reaction being substantially complete in about one minute or less. The mold is opened and a cellular cross-linked poly DCPD is recovered having a density of 0.55 grams/cc.

EXAMPLE 73

A catalyst and monomer solution is prepared by mixing under nitrogen 400 grams of DCPD, 30.7 ml of 0.1M tungsten catalyst solution, 2 grams of silica, and 57 grams of trichlorofluoromethane.

An activator and monomer solution is prepared by mixing under nitrogen 390 grams of DCPD, 39 grams of styrene-butadiene rubber, 5.49 ml of a 0.825M solution of DEAC in DCPD, 15.5 ml of a 0.450M solution of DEAI in DCPD, and 56 grams of trichlorofluoromethane.

171.4 grams of catalyst and monomer solution and 188.6 grams of activator and monomer solution were then combined and mixed under nitrogen and poured into a mold. After about one minute the mixture starts to polymerize and expand into a cellular crosslinked polymer. The final density of the foam is 0.034 grams/cc.

The silica used in Example 8 above is Cab-o-sil EH-5, manufactured by Cabot Corp.

EXAMPLE 74

A catalyst and monomer mixture is prepared by mixing under nitrogen 100 grams of DCPD, 10 grams of SDP-760 polyethylene powder (SDP-760 from Arco Chemical, 10 grams of methylene chloride, 0.50 grams of fluorinated alkyl methacrylate copolymer surfactant, and 7.56 ml of 0.1M tungsten catalyst solution.

An activator and monomer solution is prepared by mixing under nitrogen 100 grams of DCPD, 10 grams of styrene-butadiene rubber, 10 grams of methylene chloride, 0.50 grams of fluorinated alkyl methacrylate copolymer surfactant, 2.8 ml of a 0.825M solution of DEAC in DCPD, 0.53 ml of a 0.450M solution of DEAI in DCPD, and 0.70 grams of butyl ether.

The activator and monomer solution and the catalyst and monomer mixture are mixed at 40° C. and poured rapidly into a 3 inch×4 inch×9 inch mold at 45° C. where the mixture polymerizes into a cellular polymer having a density of 0.13 grams/cc.

Examples 75 and 76 preexotherm gelation of the monomer.

EXAMPLE 75

A 0.1M solution of the tungsten catalyst having a 1:1 molar ratio of $WCl_6$ to $WCl_4O$ is used. Nonyl phenol (2.21 grams, 0.01 moles) dissolved in 100 ml of toluene, that has been distilled from Na/K alloy under nitrogen, is added, and the mixture is stirred for one hour while sparging with nitrogen. Acetylacetone (2.00 grams; 0.02 moles) is then added by syringe and the mixture is stirred overnite while sparging with nitrogen to remove HCl gas.

Polymerizations are conducted in a capped 10 ml vial that has been previously sparged with nitrogen. The vial cap has five small holes in it to accommodate a gas line for flushing with nitrogen, a tube for introducing the monomer mixture, thermocouple leads to measure the exotherm of the sample during the polymerization and the spindle of a digital Brookfield viscometer to measure the viscosity of the sample during the polymerization.

A catalyst/monomer solution is prepared by mixing under nitrogen 10.0 grams of DCPD and 0.76 ml of the 0.1M catalyst solution. An activator/monomer solution is prepared by mixing under nitrogen 10.0 grams of DCPD, 0.63M solution of diethylaluminum chloride in toluene, and 0.15 grams of butyl ether.

Polymerization of DCPD is accomplished by simultaneously syringing 4.0 ml each of catalyst/monomer solution and activator/monomer solution through a T-shaped tube which is connected to the sample vial. Mixing of the two solutions is accomplished by impingement of the two streams upon each other in the T-shaped tube. After a brief induction period the viscosity of the monomer increased rapidly to greater than 100,000 centipoise. After an additional period of time a sharp exotherm is observed and a solid insoluble polymer was formed. The time that elapsed until gellation, the time until the exotherm, and the total exotherm are shown in Table 2.

EXAMPLE 76

In this example the procedure of Example 75 is followed except that 0.20 ml of a 1.12M solution of trioctylaluminum and methoxyethyl ether in DCPD was added in place of the diethylaluminum chloride and butyl ether to prepare the activator/monomer solution. A solid insoluble polymer is formed. The results are shown in Table 21.

Using the procedure of Examples 77–79 on intricate molds to form solid products.

EXAMPLE 77

This example illustrates delaying the gellation of the monomer by using a mixture of diethylaluminum chloride and diethylaluminum iodide.

The procedure of Example 75 is followed except that 0.57 ml of a 0.36M solution of diethylaluminum chloride in toluene and 0.054 ml of a 0.42M solution of diethylaluminum iodide in toluene are used in place of 0.63 ml of diethylaluminum chloride to prepare the activator/monomer solution. A solid insoluble polymer is obtained. The time until gellation, the time until exotherm, and the exotherm of the sample are given in Table 2.

EXAMPLE 78

This example illustrates delaying the gellation of the monomer by using a mixture of trioctylaluminum and diethylaluminum iodide.

The procedure of Example 75 is followed except that 0.47 ml of a solution that was 0.34M is trioctylaluminum, 0.06M in diethylaluminum iodide, and 0.40M in methoxyethyl ether in DCPD was used in place of the diethylaluminum chloride and butyl ether to make up the activator/monomer solution. A solid insoluble polymer was obtained. The time until gellation, the time until exotherm, and the exotherm of the sample are given in Table 21.

TABLE 21

| | Example | | | |
|---|---|---|---|---|
| | 75 | 76 | 77 | 78 |
| DCPD | 60.5 mmol | 60.5 mmol | 60.5 mmol | 60.5 mmol |
| Tungsten catalyst | .0303 mmol | .0303 mmol | .0303 mmol | .0303 mmol |
| Et$_2$AlCl | .0908 mmol | | .0818 mmol | |
| Octyl$_3$Al | | .0908 mmol | | |
| Et$_2$AlI | | | .00909 mmol | .0113 mmol |
| Octyl$_2$AlI | | | | |
| Butyl Ether | 0.454 mmol | | 0.454 mmol | |
| Methoxyethyl ether | | .0908 mmol | | .0756 mmol |
| Gellation time | 10 sec | 20 sec | 29 sec | 24 sec |
| Time until exotherm | 48 sec | 38 sec | 30 sec | 25 sec |
| Exotherm | 162° C. | 163° C. | 165° C. | 164° C. |

In Example 79, sufficient methoxyethyl ether is added so that the final methoxyethyl ether/alumina ratio was 3/1. In each case, a solid insoluble crosslinked polymer is obtained. The times until gellation, the times until exotherm, and the exotherms of the samples are given in Table 22. In each case, a solid insoluble cross-linked polymer is obtained. The times until gellation, the times until exotherm, and the exotherms of the samples are given in Table 22.

EXAMPLE 79

In Example 79 the procedure of Example 75 is followed except that 0.54 ml of a solution that is 0.36M in trioctylaluminum, 0.063M in dioctylaluminum iodide, and 0.42M in methoxyethyl ether in toluene is used in place of the diethylaluminum chloride and the butyl ether to make up the activator/monomer solution. A solid insoluble polymer is obtained. The time until gellation, the time until exotherm, and the exotherm of the sample are given in Table 22.

TABLE 22

| Example 79 | |
|---|---|
| DCPD | 60.5 mmol |
| Tungsten catalyst | .0303 mmol |
| Et$_2$AlCl | |
| Octyl$_3$Al | .0773 mmol |
| Et$_2$AlI | |
| Octyl$_2$AlI | .0136 mmol |
| Butyl Ether | |
| Methoxyethyl ether | .0909 mmol |
| Gellation time | 24 sec |
| Time until exotherm | 26 sec |
| Exotherm | 156° C. |

The solid insoluble polymers formed in Examples 75–79 are substantially crosslinked having notched Izod impact strengths of at least 1.5 ft-lb/in notch; a flexural moduli of at least 150,000 psi at ambient temperature (about 70° F.); and a percent gel swell determined after the polymer is immersed in toluene for two hours at 100° C. of less than about 200%.

Polymerization by the present invention may be carried out in any mold. For example, cyclic olefin monomer may be polymerized in accordance with the present invention by reaction injection molding, pour molding or spray molding.

The substantially crosslinked polymerized dicyclopentadiene of the present invention provides the beneficial flex creep properties. The weight percentage swelled in toluene is the amount of absorbed toluene as a percent by weight of the original substantially crosslinked polymerized dicyclopentadiene. The percent of flexural creep strain is the change in length of the substantially crosslinked polymerized dicyclopentadiene as a percentage of the original length of the sample tested.

The polymeric product of Example 77 has a percent gel swell of 110%. The number of monomer units between crosslinks in the polymeric product of Example 77 is about 10.

The polymeric composition of the present invention comprising substantially crosslinked polymerized units of dicyclopentadiene is preferably characterized as having a percent gel swell, determined after the polymer is immersed in toluene for two hours at 100° C., of from about 15 to about 200. More preferably, the polymeric composition of the invention is characterized as having a percent gel swell of from about 30 to about 180. Most preferably, the polymeric composition of the invention is characterized as having a percent gel swell of from about 50 to about 150.

The polymeric composition of the present invention comprising substantially crosslinked polymerized units of dicyclopentadiene is preferably characterized as having from about 1 to about 30 monomeric units between crosslinks. More preferably, the polymeric composition of the invention is characterized as having from about 2 to about 24 monomeric units being crosslinks. Most preferably, the polymeric composition of the invention is characterized as having from about 3 to about 16 monomeric units between crosslinks.

The product density may vary from about 1.2 g/ml with some filler to about 0.04 g/ml. The ultra low density foam product of the invention is novel at densities below 0.2 g/ml, for example, 0.18 g/ml and lower.

Preferably, in the substantially crosslinked polymer composition of the invention the average distance between crosslinking is preferably from about one to about 65 monomer units and more preferably from one monomer unit to about 20 monomer units. This range of crosslinking in the crosslinking polymer is characterized as having a gel swell determined after the crosslinked polymer is immersed in toluene for two hours at 100° C. of from about 15% to about 200%. Also, this range of crosslinking in the crosslinked polymer is characterized as having a flexural creep strain of from about 0.3% to about 4.5% after 100 hours of exposure to a 2000 psi stress load at 150° F.

Other features, advantages and specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What I claim and desired to protect by Letters Patent is:

1. A polymerization catalyst composition comprising:

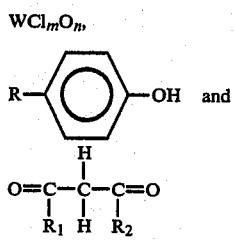

wherein R is an alkyl group having 3 to 20 carbon atoms; $R_1$ and $R_2$ are independently hydrogen, an alkyl or alkoxy of from 1 to 5 carbons; m is 4 or 6 and n is 0 or 1.

2. The composition of claim 1 wherein n is 1; m is 4 and R is nonyl and the molar ratio of $WCl_mO_n$ to

is from about 1:1 to about 1:3.

3. The composition of claim 1 further comprising a compound selected from the group consisting of 2,4-pentanedione and diglyme.

4. The composition of claim 1 further comprising a cycloolefin.

5. The composition of claim 1 further comprising a cycloolefin and the molar ratio of $WCl_mO_n$ to

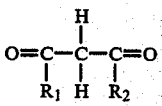

is from about 1:1 to about 1:5.

6. The composition of claim 4 wherein said cycloolefin is dicyclopentadiene said dicyclopentadiene being at least 98 percent pure prior to addition to said composition.

7. The composition of claim 5 wherein said cycloolefin is dicyclopentadiene said dicyclopentadiene being at least 98 percent pure prior to addition to said composition.

8. The catalyst composition of claim 1 wherein said $WCl_mO_n$ is a mixture of $WCl_4O$ and $WCl_6$ in a molar ratio of $WCl_4O$ to $WCl_6$ from 1:9 to 2:1.

9. A polymerization catalyst composition of the formula

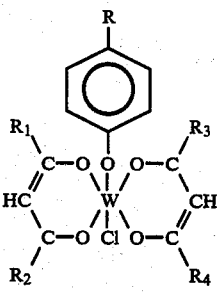

wherein R is an alkyl group of from 1 to 20 carbon atoms; $R_1$ is hydrogen or an alkyl group of from 1 to 5 carbon atoms; $R_2$ is hydrogen or an alkyl group of from 1 to 5 carbon atoms; $R_3$ is hydrogen or an alkyl group of from 1 to 5 carbon atoms; $R_4$ is hydrogen or an alkyl group of from 1 to 5 carbon atoms.

10. The composition of claim 9 further comprising a cycloolefin.

11. The composition of claim 10 wherein said cycloolefin is dicyclopentadiene.

12. A polymerization catalyst composition comprising:

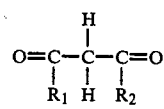

wherein m is 4 or 6; n is 0 or 1; and $R_1$ and $R_2$ are independently hydrogen, an alkyl or alkoxy of from 1 to 5 carbons.

13. The composition of claim 12 wherein n is 1 and m is 4.

14. The composition of claim 13 further comprising a cycloolefin and wherein the molar ratio of $WCl_mO_n$ to

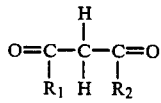

is from about 1:1 to about 1:5.

15. The composition of claim 14 wherein said cycloolefin is dicyclopentadiene, said dicyclopentadiene being at least 98 percent pure prior to addition to said composition.

* * * * *